US012668635B1

(12) United States Patent
Karakunnel

(10) Patent No.: US 12,668,635 B1
(45) Date of Patent: Jun. 30, 2026

(54) METHODS OF TREATING SOLID TUMORS USING AN ANTI-PD-1 ANTIBODY OR A FRAGMENT THEREOF

(71) Applicant: Arcus Biosciences, Inc., Hayward, CA (US)

(72) Inventor: Joyson J. Karakunnel, Potomac, MD (US)

(73) Assignee: Arcus Biosciences, Inc., Hayward, CA (US)

( * ) Notice: Subject to any disclaimer, the term of this patent is extended or adjusted under 35 U.S.C. 154(b) by 462 days.

(21) Appl. No.: 18/047,617

(22) Filed: Oct. 18, 2022

Related U.S. Application Data

(63) Continuation of application No. 17/692,482, filed on Mar. 11, 2022, now abandoned, which is a continuation of application No. 17/377,663, filed on Jul. 16, 2021, now abandoned, which is a continuation of application No. 16/197,134, filed on Nov. 20, 2018, now abandoned.

(60) Provisional application No. 62/589,501, filed on Nov. 21, 2017.

(51) Int. Cl.
*A61P 35/00* (2006.01)
*A61K 9/00* (2006.01)
*C07K 16/28* (2006.01)

(52) U.S. Cl.
CPC ........ *C07K 16/2827* (2013.01); *A61K 9/0019* (2013.01); *A61P 35/00* (2018.01); *C07K 2317/565* (2013.01)

(58) Field of Classification Search
CPC .......... C07K 16/2827; C07K 2317/565; A61K 9/0019; A61P 35/00
USPC ...................................................... 424/133.1
See application file for complete search history.

(56) References Cited

U.S. PATENT DOCUMENTS

| | | | |
|---|---|---|---|
| RE30,985 E | 6/1982 | Cartaya | |
| 4,560,655 A | 12/1985 | Baker | |
| 4,657,866 A | 4/1987 | Kumar | |
| 4,767,704 A | 8/1988 | Cleveland et al. | |
| 4,927,762 A | 5/1990 | Darfler | |
| 5,122,469 A | 6/1992 | Mather et al. | |
| 6,005,079 A | 12/1999 | Casterman et al. | |
| 7,595,048 B2 | 9/2009 | Honjo et al. | |
| 7,638,492 B2 | 12/2009 | Wood et al. | |
| 7,851,598 B2 | 12/2010 | Davis | |
| 7,892,540 B2 | 2/2011 | Chen et al. | |
| 7,943,743 B2 | 5/2011 | Korman et al. | |
| 8,008,449 B2 | 8/2011 | Korman et al. | |
| 8,168,179 B2 | 5/2012 | Honjo et al. | |
| 8,354,509 B2 | 1/2013 | Carven et al. | |
| 8,460,886 B2 | 6/2013 | Shibayama et al. | |
| 8,728,474 B2 | 5/2014 | Honjo et al. | |

| | | | |
|---|---|---|---|
| 8,747,833 B2 | 6/2014 | Chen et al. | |
| 8,779,105 B2 | 7/2014 | Korman et al. | |
| 8,907,157 B2 | 12/2014 | Buelow | |
| 8,945,561 B2 | 2/2015 | Davis | |
| 8,952,136 B2 | 2/2015 | Carven et al. | |
| 9,067,999 B1 | 6/2015 | Honjo et al. | |
| 9,073,994 B2 | 7/2015 | Honjo et al. | |
| 9,084,776 B2 | 7/2015 | Korman et al. | |
| 9,358,289 B2 | 6/2016 | Korman et al. | |
| 9,387,247 B2 | 7/2016 | Korman et al. | |
| 9,393,301 B2 | 7/2016 | Honjo et al. | |
| 9,402,899 B2 | 8/2016 | Honjo et al. | |
| 9,439,962 B2 | 9/2016 | Honjo et al. | |
| 9,492,539 B2 | 11/2016 | Korman et al. | |
| 9,492,540 B2 | 11/2016 | Korman et al. | |
| 9,803,015 B2 | 10/2017 | Chen et al. | |
| 9,856,320 B2 | 1/2018 | Cogswell et al. | |
| 10,087,251 B2 | 10/2018 | Hermans et al. | |
| 10,323,093 B2 | 6/2019 | Cogswell et al. | |
| 10,441,655 B2 | 10/2019 | Korman et al. | |
| 10,512,689 B2 | 12/2019 | Sadineni et al. | |
| 10,544,224 B2 | 1/2020 | Manekas et al. | |
| 10,604,575 B2 | 3/2020 | Cogswell et al. | |
| 11,008,391 B2 | 5/2021 | Zheng et al. | |
| 11,643,465 B2 | 5/2023 | Zheng et al. | |
| 2014/0212422 A1 | 7/2014 | Korman et al. | |
| 2015/0203579 A1 | 7/2015 | Papadopoulos et al. | |
| 2016/0304607 A1 | 10/2016 | Sadineni et al. | |
| 2017/0037132 A1 | 2/2017 | Manekas et al. | |
| 2017/0158776 A1 | 6/2017 | Feltquate et al. | |
| 2018/0155429 A1 | 6/2018 | Finckenstein | |
| 2018/0162942 A1 | 6/2018 | Simon et al. | |
| 2018/0244781 A1 | 8/2018 | Cuillerot et al. | |
| 2018/0346569 A1 | 12/2018 | Wang et al. | |
| 2019/0112377 A1 | 4/2019 | Cogswell et al. | |
| 2019/0144542 A1 | 5/2019 | Galler et al. | |

(Continued)

FOREIGN PATENT DOCUMENTS

| | | |
|---|---|---|
| CN | 101213297 | 7/2008 |
| CN | 101526890 | 9/2009 |

(Continued)

OTHER PUBLICATIONS

Adderson et al., NCBI GenBank database, Accession No. AAA59031.1 immunoglobulin lambda-chain, partial [*Homo sapiens*], Jan. 5, 1995, 1 page.

(Continued)

*Primary Examiner* — Yan Xiao

(74) *Attorney, Agent, or Firm* — Sheppard Mullin Richter & Hampton LLP

(57) ABSTRACT

Provided herein are methods of treating solid tumors comprising administering to a subject in need thereof a therapeutically effective amount of the anti-PD-1 antibodies or the antigen-binding fragments thereof described herein.

18 Claims, 2 Drawing Sheets

Specification includes a Sequence Listing.

(56) References Cited

U.S. PATENT DOCUMENTS

| | | |
|---|---|---|
| 2019/0194328 A1 | 6/2019 | Yang |
| 2019/0263923 A1 | 8/2019 | Jure-kunkel et al. |
| 2019/0367616 A1 | 12/2019 | Lantto et al. |
| 2020/0002420 A1 | 1/2020 | Zheng et al. |
| 2020/0010549 A1 | 1/2020 | Yang et al. |
| 2020/0010550 A1 | 1/2020 | Rietschel et al. |

FOREIGN PATENT DOCUMENTS

| | | |
|---|---|---|
| CN | 101763842 | 6/2010 |
| CN | 102131828 | 7/2011 |
| CN | 102737616 | 10/2012 |
| CN | 103242448 | 8/2013 |
| CN | 103701643 | 4/2014 |
| CN | 105336289 | 2/2016 |
| CN | 205017477 | 2/2016 |
| CN | 103608040 | 3/2017 |
| CN | 104250302 | 11/2017 |
| CN | 104479018 | 9/2018 |
| CN | 104479020 | 8/2019 |
| EP | 0402226 | 12/1990 |
| EP | 0404097 | 12/1990 |
| EP | 0183070 | 10/1991 |
| EP | 0244234 | 11/2001 |
| EP | 2152880 | 8/2011 |
| EP | 2360254 | 8/2011 |
| EP | 2336329 | 10/2012 |
| EP | 2857420 | 4/2015 |
| EP | 1810026 | 4/2018 |
| JP | 2006521783 | 9/2006 |
| JP | 2009155338 | 7/2009 |
| JP | 2010500872 | 1/2010 |
| WO | WO-8700195 | 1/1987 |
| WO | WO-9003430 | 4/1990 |
| WO | WO-9311161 | 6/1993 |
| WO | WO-9404678 | 3/1994 |
| WO | WO-9425591 | 11/1994 |
| WO | WO-0114557 | 3/2001 |
| WO | WO-2004004771 | 1/2004 |
| WO | WO-2004056875 | 7/2004 |
| WO | WO-2005066867 | 7/2005 |
| WO | WO-2006042237 | 4/2006 |
| WO | WO-2006121168 | 11/2006 |
| WO | WO-2006133396 | 12/2006 |
| WO | WO-2008007144 | 1/2008 |
| WO | WO-2008071447 | 6/2008 |
| WO | WO-2008112003 | 9/2008 |
| WO | WO-2008156712 | 12/2008 |
| WO | WO-2010001617 | 1/2010 |
| WO | WO-2010063011 | 6/2010 |
| WO | WO-2012056407 | 5/2012 |
| WO | WO-2013059524 | 4/2013 |
| WO | WO-2013168327 | 11/2013 |
| WO | WO-2013173223 | 11/2013 |
| WO | WO-2014194302 | 12/2014 |
| WO | WO-2015134605 | 9/2015 |
| WO | WO-2015176033 | 11/2015 |
| WO | WO-2016007235 | 1/2016 |
| WO | WO-2016100561 | 6/2016 |
| WO | WO-2016137985 | 9/2016 |
| WO | WO-2016144673 | 9/2016 |
| WO | WO-2016168716 | 10/2016 |
| WO | WO-2016176503 | 11/2016 |
| WO | WO-2016176504 | 11/2016 |
| WO | WO-2016191751 | 12/2016 |
| WO | WO-2016196389 | 12/2016 |
| WO | WO-2017011666 | 1/2017 |
| WO | WO-2017019896 | 2/2017 |
| WO | WO-2017025051 | 2/2017 |
| WO | WO-2017055547 | 4/2017 |
| WO | WO-2017087599 | 5/2017 |
| WO | WO-2017132508 | 8/2017 |
| WO | WO-2017176925 | 10/2017 |
| WO | WO-2017210453 | 12/2017 |
| WO | WO-2017210624 | 12/2017 |
| WO | WO-2017210637 | 12/2017 |
| WO | WO-2018053709 | 3/2018 |
| WO | WO-2018081621 | 5/2018 |
| WO | WO-2018091661 | 5/2018 |
| WO | WO-2018132287 | 7/2018 |
| WO | WO-2018156494 | 8/2018 |
| WO | WO-2018183928 | 10/2018 |
| WO | WO-2018204368 | 11/2018 |
| WO | WO-2018223040 | 12/2018 |
| WO | WO-2019023624 | 1/2019 |
| WO | WO-2019062642 | 4/2019 |
| WO | WO-2019075468 | 4/2019 |
| WO | WO-2019080872 | 5/2019 |

OTHER PUBLICATIONS

Al-Lazikani et al., "Standard conformations for the canonical structures of immunoglobulins," J. Mol. Biol., 1997, 273(4):927-948.

Altschul et al, "Basic local alignment search tool," J. Mol. Biol., 1990, 215:403-410.

Altschul et al., "Gapped BLAST and PSI-BLAST: a new generation of protein database search programs," Nucleic Acids Res, 1997, 25:3389-3402.

Barnes et al., "Methods for growth of cultured cells in serum-free medium," Anal. Biochem., 1980, 102:255-270.

Bendig, "Humanization of rodent monoclonal antibodies by CDR grafting", Methods: A Companion to Methods in Enzymology, 1995, 8:83-93.

Cappelli et al., "Inflammatory arthritis and sicca syndrome induced by nivolumab and ipilimumab", Ann Rheum Disease, 2016, 0:1-8.

Carter et al., "High level Escherichia coli expression and production of a bivalent humanized antibody fragment," Bio/Technology, 1992, 10:163-167.

Chen et al, "Enhancement and destruction of antibody function by somatic mutation: unequal occurrence is controlled by V gene combinatorial associations", The EMBO Journal, 1995, 14(12):2784-2794.

Chien et al., "Significant structural and functional change of an antigen-binding site by a distant amino acid substitution: Proposal of a structural mechanism", Proc. Natl. Acad. Sci, Jul. 1989, 86:5532-5536.

Chothia et al., "Canonical structures for the hypervariable regions of immunoglobulins," J.Mol.Biol., 1987, 196(4):901-917.

Chothia et al., "Conformations of immunoglobulin hypervariable regions,"Nature., 1989, Dec. 21, 28;342(6252):877-883.

Chothia et al., "Domain association in immunoglobulin molecules. The packing of variable domains," J Mol Biol., 1985, 186(3):651-663.

Dahan et al., "TCR-like antibodies distinguish conformational and functional differences in two versus four-domain auto reactive MHC class II-peptide complexes," Eur J Immunol., 2011, 41:1465-1479, Author Manuscript, 26 pages.

Extended European Search Report mailed on Feb. 28, 2019, for EP Patent Application No. 16834675.7, 16 pages.

Flisikowska et al., "Efficient immunoglobulin gene disruption and targeted replacement in rabbit using zinc finger nucleases," PLoS One, 2011, 6:e21045, 10 pages.

Freeman et al., "Engagement of the PD-1 immunoinhibitory receptor by a novel B7 family member leads to negative regulation of lymphocyte activation," J Exp. Med, 2000, 192:1027-1034.

GenBank Accession No. AEZ52328.1, "Immunoglobulin alpha heavy chain variable region, partial[Homo sapiens]", May 31, 2012, retrieved on Jul. 16, 2021, retrieved from ncbi.nlm.nih.gov/protein/AEZ52328.1.

Geurts et al., "Knockout Rats via Embryo Microinjection of Zinc-Finger Nucleases", Science, 2009, 325(5939):433. 1 page.

Geurts et al., "Knockout Rats Produced Using Designed Zinc Finger Nucleases", Author Manuscript, Science, 2009, 325(5939):433. 3 pages.

Graham et al., "Characteristics of a human cell line transformed by DNA from human adenovirus type 5," J. Gen Virol., 1977, 36:59-72.

(56)                   References Cited

OTHER PUBLICATIONS

Griffiths et al., "Human anti-self antibodies with high specificity from phage display libraries", The EMBO Journal, 1993, 12(2):725-734.

Guss et al., "Structure of the IgG-binding regions of streptococcal protein G," EMBO J., 1986, 5:1567-1575.

Ham et al., "Media and growth requirements," Methods in Enzymology, 1979, 58:44-93.

Hamers-Casterrnan et al., "Naturally occurring antibodies devoid of light chains," Nature, 1993, 363(6428):446-448.

Hao et al., "Epitope characterization of an anti-PD-L1 antibody using orthogonal approaches," Molecular Recognition, 2015, 28:269-276.

Higgins et al., "[22] Using CLUSTAL for multiple sequence alignments", Methods in Enzymology, 1996, 266:383-402.

Holliger et al., "Diabodies": small bivalent and bispecific antibody fragments, Proc Natl Acad Sci USA, 1993, 90(14):6444-6448.

Huston et al., "Protein engineering of antibody binding sites: recovery of specific activity in an anti-digoxin single-chain Fv analogue produced in *Escherichia coli*," Proc. Natl Acad Sci USA, 1988, 85:5879-5883.

Ignatovich et al., NCBI GenBank database, Accession No. AAF20468.1, immunoglobulin lambda light chain variable region, partial [*Homo sapiens*], pri Jul. 26, 2016, 1 page.

Ignatovich et al., NCBI GenBank database, Accession No. AAF20469.1, immunoglobulin lambda light chain variable region, partial [*Homo sapiens*], pri Jul. 26, 2016, 1 page.

International Preliminary Report on Patentability for International Application No. PCT/CN2016/094624 dated Feb. 13, 2018. 6 pages.

International Search Report and Written Opinion for International Application No. PCT/CN2016/094624 dated Nov. 3, 2016. 13 pages.

Ishida et al., "Production of human monoclonal and polyclonal antibodies in TransChromo animals," Cloning and Stem Cells, 2002, 4:91-102.

Koch-Nolte et al., "Single domain antibodies from llama effectively and specifically block T cell ecto-ADP-ribosyltransferase ART2.2 in vivo," FASEB J., 2007, 21(13):3490-3498.

Kussie et al., "A Single Engineered Amino Acid Substitution Changes Antibody Fine Specificity", Journal of Immunology, 1994, 152:146-152.

Larkin et al, "Clustal Wand Clustal X version 2.0," Bioinformatics, 2007, 23(21):2947-2948.

Lee et al., "Complete humanization of the mouse immunoglobulin loci enables efficient therapeutic antibody discovery," Nat Biotechnol, 2014, 12 pages.

Lindmark et al., "Binding of immunoglobulins to protein A and immunoglobulin levels in mammalian sera," J. Immunol. Meth., 1983, 62:1-13.

Lonberg et al., "Antigen-specific human antibodies from mice comprising four distinct genetic modifications," Nature, 1994, 368(6474): 856-859.

Ma et al., "Human antibody expression in transgenic rats: comparison of chimeric IgH loci with human VH, D and JH but bearing different rat C-gene regions," Journal of Immunological Methods, 2013, 400-401:78-86.

Mather et a., "Culture of testicular cells in hormone-supplemented serum-free medium," Annals NY. Acad. Sci., 1982, 383:44-68.

Mather, "Establishment and characterization of two distinct mouse testicular epithelial cell lines," Biol. Reprod., 1980, 23:243-252.

McDermott et al., "PD-1 as a potential target in cancer therapy", Cancer Medicine, 2013, 2(5):662-673.

Mendez et al., "Functional transplant of megabase human immunoglobulin loci recapitulates human antibody response in mice," Nat Genet., 1997, 15:146-156.

Murphy et al., "Mice with megabase humanization of their immunoglobulin genes generate antibodies as efficiently as normal mice," Proc Natl Acad Sci USA, 2014, 111:5153-5158.

Muyldermans et al., "Single domain camel antibodies: current status," J. Biotechnol., 2001, 74(4):277-302.

NCBI accession No. N, P 054862.1, "Programmed cell death 1 ligand 1 isoform a precursor [*Homo sapiens*]", Jul. 11, 2021, 4 pages.

NCBI accession No. NM_005018.2, "Programmed cell death 1 ligand 1 isoform a precursor [*Homo sapiens*]", Jul. 11, 2021, 4 pages.

NCBI accession No. NM_014143.3, "*Homo sapiens* CD274 molecule (CD274), transcript variant 1, mRNA", Oct. 14, 2018, 5 pages.

NCBI accession No. NP_ 005009.2, "Programmed cell death protein 1 precursor [*Homo sapiens*] ", Jul. 5, 2021, 4 pages.

Nguyen et al. "Heavy-chain antibodies in Camelidae; a case of evolutionary innovation," Immunogenetics 2002, 54(1):39-47.

Nguyen et al., "Heavy-chain only antibodies derived from dromedary are secreted and displayed by mouse B cells," Immunology, 2003, 109(1):93-101.

Osborn et al., "High-affinity IgG antibodies develop naturally in Ig-knockout rats carrying germline human IgH/Igκ/Igλ loci bearing the rat $C_H$ region," Journal of immunology, 2013, 190:1481-1490.

Pal et al., NCBI GenBank database, Accession No. AA047766.1, immunoglobulin lambda light chain VLJ region, partial [*Homo sapiens*], pri Jul. 25, 2016, 2 pages.

Partial Supplementary European Search Report mailed on Dec. 11, 2018, for EP Patent Application No. 16834675.7, 15 pages.

Paul, Fundamental Immunology, 3rd Edition, 1993, pp. 292-295.

PCT International Preliminary Report on Patentability in International Application No. PCT/CN2015/086594, dated Feb. 13, 2018, 9 pages.

PCT International Search Report and Written Opinion in International Application No. PCT/CN2015/086594, dated May 18, 2016, 15 pages.

Perez De La Lastra et al., "Epitope mapping of 10 monoclonal antibodies against the pig analogue of human membrane cofactor protein (MCP)," Immunology, Apr. 1999, 96(4 ):663-670.

Riechmann et al., "Single domain antibodies: comparison of camel VH and camelised human VH domains," J Immunol Methods., 1999, 231(1-2):25-38.

Rudikoff et al., "Single amino acid substitution altering antigen-binding specificity", PNAS, 1982, 79:1979-1983.

Topalian et al., "Safety, Activity, and Immune Correlations of Anti-PD-1 Antibody in Cancer", The New England Journal of Medicine, 2012, 366(26):2443-2454.

Urlaub et al., "Isolation of Chinese hamster cell mutants deficient in dihydrofolate reductase activity," Proc. Natl. Acad. Sci. USA, 1980, 77:4216-4220.

Agata et al., Expression of the PD-1 antigen on the surface of stimulated mouse T and B lymphocytes, International Immunology, 1996, vol. 8, No. 5, pp. 765-772.

Bavencio (avelumab) injection, for intravenous use, New York, NY: EMD Serono, Inc and Pfizer, Inc.; May 2017.

Bennett et al., Program Death-1 Engagement Upon TCR Activation has Distinct Effects on Costimulation and Cytokine-driven Proliferation: Attenuation of ICOS, IL-4, and IL-21, But Not CD28, IL-7, and IL-15 Responses, Journal of Immunology, 2003, 170:711-8.

Blank et al. Interaction of PD-L1 on tumor cells with PD-1 on tumor specific T cells as a mechanism of immune evasion: implications for tumor immunotherapy, Cancer Immunology Immunother, 2005, 54:307-14.

Carter et al., PD-1: Pd-L inhibitory pathway affects both CD4+ and CD8+ T cells and is overcome by IL-2, Eur J Immunol, 2002, 32:634-43.

Dong et al., Tumor-associated B7-H1 promotes T-cell apoptosis: A potential mechanism of immune evasion, Nature Medicine, Aug. 2002, 8:793-800.

Dong et al., B7-H1 pathway and its role in the evasion of tumor immunity, J Mol Med (Berl), 2003, 81:281-287.

Eisenhauer et al., New response evaluation criteria in solid tumors: Revised RECIST guidelines (version 1.1), European Journal of Cancer, 2009, 45:228-247.

(56) References Cited

OTHER PUBLICATIONS

Food and Drug Administration (FDA), Modification of the Dosage Regimen for Nivolumab, Sep. 13, 2016. Available at https://www.fda.gov/drugs/informationondrugs/approveddrugs/ucm520871.htm.

Freeman et al., Engagement of the PD-1 Immunoinhibitory Receptor by a Novel B7 Family Member Leads to Negative Regulation of Lymphocyte Activation, J Exp Med., Oct. 2, 2000, vol. 192, No. 7, pp. 1027-1034.

Imfinzi (durvalaumab) injection, for intravenous use, Wilmington, DE: AstraZeneca Pharmaceuticals LP; Apr. 2017.

Keytruda (pembrolizumab) for injection for intraveous use, Whitehouse Station, NJ: Merck Sharpe & Dohme Corp., a subsidiary of Merck & Co, Inc. May 2014.

METHODS OF TREATING SOLID TUMORS USING AN ANTI-PD-1 ANTIBODY OR A FRAGMENT THEREOF

CROSS-REFERENCES TO RELATED APPLICATIONS

This application is a continuation application of U.S. Ser. No. 17/692,482, filed Mar. 11, 2022, now abandoned, which is a continuation application of U.S. Ser. No. 17/377,663, filed Jul. 16, 2021, now abandoned, which is a continuation of U.S. Ser. No. 16/197,134, filed Nov. 20, 2018, now abandoned, which claims benefit under 35 U.S.C. § 119(e) of U.S. Provisional Application No. 62/589,501, filed Nov. 21, 2017, which are incorporated herein by reference in their entireties.

STATEMENT AS TO RIGHTS TO INVENTIONS MADE UNDER FEDERALLY SPONSORED RESEARCH AND DEVELOPMENT

NOT APPLICABLE

REFERENCE TO AN ELECTRONIC SEQUENCE LISTING

The contents of the electronic sequence listing (P0010-US3_2022-10-12 Sequence Listing.xml; Size: 66,570 bytes; and Date of Creation: Oct. 12, 2022) are herein incorporated by reference in their entireties.

BRIEF SUMMARY OF THE INVENTION

Provided herein are methods of treating solid tumors comprising administering to a subject in need thereof a therapeutically effective amount of the anti-PD-1 antibodies or the antigen-binding fragments thereof described herein.

DETAILED DESCRIPTION OF THE INVENTION

I. Definitions

Figure 1:
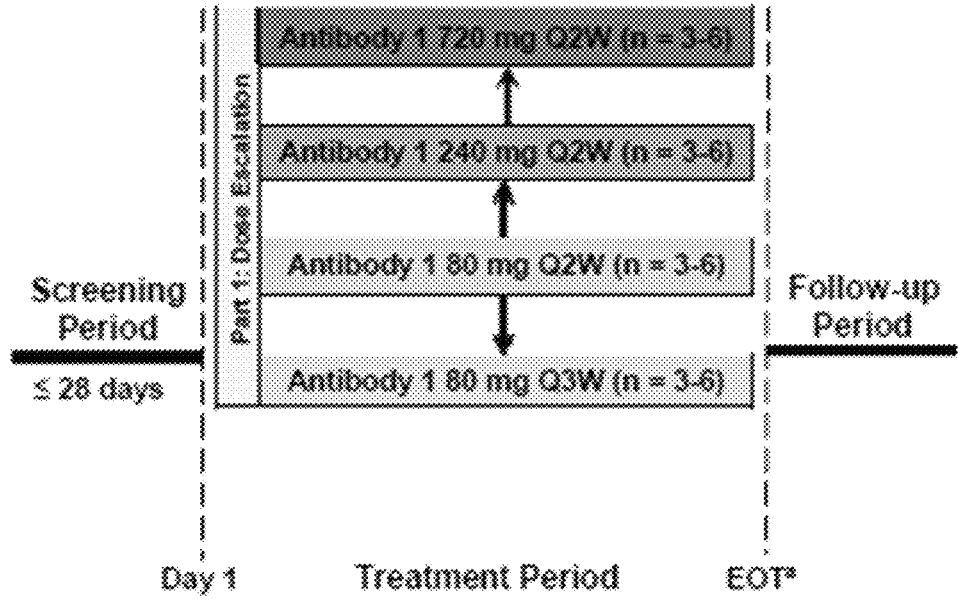
FIG. 1 illustrates the study design for the Phase I clinical trial. EOT=end of treatment; PD=pharmacodynamics; PK=pharmacokinetics; Q2W=every 2 weeks; Q3W=every 3 weeks. $^a$End of Treatment refers to the time point when treatment with Antibody 1 is stopped due to progressive disease, unacceptable toxicity, withdrawal of consent, or other reasons for study drug discontinuation.

The term "antibody" as used herein includes any immunoglobulin, monoclonal antibody, polyclonal antibody, multispecific antibody, or bispecific (bivalent) antibody that binds to a specific antigen. A native intact antibody comprises two heavy chains and two light chains. Each heavy chain consists of a variable region and a first, second, and third constant region, while each light chain consists of a variable region and a constant region. Mammalian heavy chains are classified as α, δ, ε, γ, and μ, and mammalian light chains are classified as λ or κ. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variables region in both chains generally contain three highly variable loops called the complementarity determining regions (CDRs) (light (L) chain CDRs including LCDR1, LCDR2, and LCDR3, heavy (H) chain CDRs including HCDR1, HCDR2, HCDR3). CDR boundaries for the antibodies and antigen-binding fragments disclosed herein may be defined or identified by the conventions of Kabat, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J. Mol. Biol., 196,901 (1987); Chothia, C. et al., Nature. December 21-28; 342(6252):877-83 (1989); Kabat E. A. et al., National Institutes of Health, Bethesda, Md. (1991)). The three CDRs are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "Antibody 1" refers to a fully human immunoglobulin G4 (IgG4) monoclonal antibody targeting human PD-1. Antibody 1 comprises 2 heavy chains of the IgG4 subclass and 2 light chains of the lambda subclass. Antibody 1 has a heavy chain variable region comprising SEQ ID NO: 53; and a light chain variable region comprising SEQ ID NO: 67.

The term "antigen-binding fragment" as used herein refers to an antibody fragment formed from a portion of an antibody comprising one or more CDRs, or any other antibody fragment that binds to an antigen but does not comprise an intact native antibody structure. "Fab" with regard to an antibody refers to that portion of the antibody consisting of a single light chain (both variable and constant regions) bound to the variable region and first constant region of a single heavy chain by a disulfide bond.

The term "fully human" as used herein, with reference to antibody or antigen-binding fragment, means that the antibody or the antigen-binding fragment has or consists of amino acid sequence(s) corresponding to that of an antibody produced by a human or a human immune cell, or derived from a non-human source such as a transgenic non-human animal that utilizes human antibody repertoires or other human antibody-encoding sequences. In certain embodiments, a fully human antibody does not comprise amino acid residues (in particular antigen-binding residues) derived from a non-human antibody.

"PD-1" as used herein refers programmed cell death protein, which belongs to the superfamily of immunoglobulin and functions as coinhibitory receptor to negatively regulate the immune system. PD-1 is a member of the CD28/CTLA-4 family, and has two known ligands including PD-L1 and PD-L2. Representative amino acid sequence of human PD-I is disclosed under the NCBI accession number: NP_005009.2, and the representative nucleic acid sequence encoding the human PD-I is shown under the NCBI accession number: NM_005018.2.

"PD-L1" as used herein refers to programmed cell death ligand 1 (PD-L1, see, for example, Freeman et al. (2000) *J. Exp. Med.* 192:1027). Representative amino acid sequence of human PD-L1 is disclosed under the NCBI accession number: NP_054862.1, and the representative nucleic acid sequence encoding the human PD-L1 is shown under the NCBI accession number: NM_014143.3. PD-L1 is expressed in placenta, spleen, lymph nodes, thymus, heart, fetal liver, and is also found on many tumor or cancer cells. PD-L1 binds to its receptor PD-1 or B7-1, which is expressed on activated T cells, B cells and myeloid cells. The binding of PD-L1 and its receptor induces signal transduction to suppress TCR-mediated activation of cytokine production and T cell proliferation. Accordingly, PD-L1 plays a major role in suppressing immune system during particular events such as pregnancy, autoimmune diseases, tissue allografts, and is believed to allow tumor or cancer cells to circumvent the immunological checkpoint and evade the immune response.

"Anti-PD-1 antibody" as used herein refers to an antibody that is capable of specific binding to PD-1 (e.g. human or monkey PD-1) with an affinity which is sufficient to provide for diagnostic and/or therapeutic use.

"1.7.3 hAb" as used herein refers to a fully human monoclonal antibody having a heavy chain variable region of SEQ ID NO: 45, light chain variable region of SEQ ID NO: 47, and a human constant region of IgG4 isotype.

"1.49.9 hAb" as used herein refers to a fully human monoclonal antibody having a heavy chain variable region of SEQ ID NO: 49, light chain variable region of SEQ ID NO: 51, and a human constant region of IgG4 isotype.

"1.103.11 hAb" as used herein refers to a fully human monoclonal antibody having a heavy chain variable region of SEQ ID NO: 53, light chain variable region of SEQ ID NO: 55, and a human constant region of IgG4 isotype.

"1.103.11-v2 hAb" as used herein refers to a fully human monoclonal antibody having a heavy chain variable region of SEQ ID NO: 53, light chain variable region of SEQ ID NO: 67, and a human constant region of IgG4 isotype.

"1.139.15 hAb" as used herein refers to a fully human monoclonal antibody having a heavy chain variable region of SEQ ID NO: 57, light chain variable region of SEQ ID NO: 59, and a human constant region of IgG4 isotype.

"1.153.7 hAb" as used herein refers to a fully human monoclonal antibody having a heavy chain variable region of SEQ ID NO: 61, light chain variable region of SEQ ID NO: 63, and a human constant region of IgG4 isotype.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

"T cell" as used herein includes CD4$^+$ T cells, CD8$^+$ T cells, T helper 1 type T cells, T helper 2 type T cells, T helper 17 type T cells and inhibitory T cells.

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis.

"Cancer" or "cancerous condition" as used herein refers to any medical condition mediated by neoplastic or malignant cell growth, proliferation, or metastasis, and includes both solid cancers and non-solid cancers such as leukemia. "Tumor" as used herein refers to a solid mass of neoplastic and/or malignant cells.

The terms "subject", "patient" or "individual" are used herein interchangeably to include a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance. In some embodiments, the subject is a human.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof. With regard to cancer, "treating" or "treatment" may refer to inhibiting or slowing neoplastic or malignant cell growth, proliferation, or metastasis, preventing or delaying the development of neoplastic or malignant cell growth, proliferation, or metastasis, or some combination thereof. With regard to a tumor, "treating" or "treatment" includes eradicating all or part of a tumor, inhibiting or slowing tumor growth and metastasis, preventing or delaying the development of a tumor, or some combination thereof.

A "disease associated with or related to PD-1" as used herein refers to any condition that is caused by, exacerbated by, or otherwise linked to increased or decreased expression or activities of PD-1 (e.g. a human PD-1).

The term "therapeutically effective amount" or "effective dosage" as used herein refers to the dosage or concentration of a drug effective to treat a disease or condition associated with human PD-1. For example, with regard to the use of the antibodies or antigen-binding fragments disclosed herein to treat cancer, a therapeutically effective amount is the dosage or concentration of the antibody or antigen-binding fragment capable of eradicating all or part of a tumor, inhibiting or slowing tumor growth, inhibiting growth or proliferation of cells mediating a cancerous condition, inhibiting tumor cell metastasis, ameliorating any symptom or marker associated with a tumor or cancerous condition, preventing or delaying the development of a tumor or cancerous condition, or some combination thereof.

The term "solid tumor" refers to neoplasias, carcinoma, or metastases that typically aggregate together and form a mass. Solid tumors are tumors of body tissues other than blood, bone marrow, and lymphoid system. Exemplary solid tumors include, but are not limited to, lung carcinoma, breast carcinoma, ovarian carcinoma, skin carcinoma, colon carcinoma, urinary bladder carcinoma, liver carcinoma, gastric carcinoma, prostate cancer, pancreatic cancer, renal cell carcinoma, nasopharyngeal carcinoma, squamous cell carcinoma, thyroid papillary carcinoma, cervical carcinoma, small cell lung carcinoma, non-small cell lung carcinoma, head and neck squamous cell cancer and sarcomas.

The term "advanced solid tumor" refers to refers to solid tumors which are metastatic, recurrent, or tumors which have not responded to one or more previously administered cancer therapeutics.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

II. Detailed Description of Embodiments

A. Anti-PD-1 Antibodies for Use

In one aspect, the present disclosure provides methods of using anti-PD-1 antibodies and the antigen-binding fragments thereof. PD-1, also called as CD279, is known as a key immune-checkpoint receptor expressed by activated T cells, which mediates immunosuppression. PD-1 ligand i (PD-Li) is a 40 kDa transmembrane protein expressed on various tumor cells, stromal cells or both, and binds to PD-1. Inhibition of the interaction between PD-1 and PD-Li can enhance T-cell responses and thus mediates anti-cancer activity.

In certain embodiments, the present disclosure provides methods of using exemplary fully human monoclonal antibodies i.7.3 hAb, i.49.9 hAb, 1.103.ii hAb, 1.103.ii-v2 hAb, 1.139.i5 hAb, and 1.153.7 hAb, whose CDR sequences are shown in the below Table i, and heavy or light chain variable region sequences are also shown below.

TABLE 1

| | CDR1 | CDR2 | CDR3 |
|---|---|---|---|
| 1.7.3 hAb - VH(23466-VH) | SEQ ID NO: 1 STTYYWV SEQ ID NO: 2 AGT ACT ACT TAC TAC TGG GTC | SEQ ID NO: 3 SISYSGNTYYNPSLKS SEQ ID NO: 4 AGT ATC TCT TAT AGT GGG AAC ACC TAC TAC AAT CCG TCC CTC AAG AGT | SEQ ID NO: 5 HLGYNGRYLPFDY SEQ ID NO: 6 CAT CTA GGG TAT AAT GGG AGG TAC CTC CCC TTT GAC TAC |
| 1.7.3 hAb - VL(23195-VL) | SEQ ID NO: 7 TGTSSDVGFYNYVS SEQ ID NO: 8 ACT GGA ACC AGC AGT GAC GTT GGT TTT TAT AAC TAT GTC TCC | SEQ ID NO: 9 DVTNRPS SEQ ID NO: 10 GAT GTC ACT AAT CGG CCC TCA | SEQ ID NO: 11 SSYTSISTWV SEQ ID NO: 12 AGC TCA TAT ACA AGC ATC AGC ACT TGG GTG |
| 1.49.9 hAb - VH(20951-VH) | SEQ ID NO: 13 SSTYYWG SEQ ID NO: 14 AGT AGT ACT TAC TAC TGG GGC | SEQ ID NO: 15 SISYSGSTYYNPSLKS SEQ ID NO: 16 AGT ATC TCT TAT AGT GGG AGC ACC TAC TAC AAT CCG TCC CTC AAG AGT | SEQ ID NO: 5 HLGYNGRYLPFDY SEQ ID NO: 6 CAT CTA GGG TAT AAT GGG AGG TAC CTC CCC TTT GAC TAC |
| 1.49.9 hAb - VH(20951-VL) | SEQ ID NO: 7 TGTSSDVGFYNYVS SEQ ID NO: 8 ACT GGA ACC AGC AGT GAC GTT GGT TTT TAT AAC TAT GTC TCC | SEQ ID NO: 17 DVSNRPS SEQ ID NO: 18 GAT GTC AGT AAT CGG CCC TCA | SEQ ID NO11 SSYTSISTWV SEQ ID NO: 12 AGC TCA TAT ACA AGC ATC AGC ACT TGG GTG |

TABLE 1-continued

|  | CDR1 | CDR2 | CDR3 |
|---|---|---|---|
| 1.103.11<br>hAb -<br>VH(20975-<br>VH) | SEQ ID NO: 1<br>STTYYWV<br>SEQ ID NO: 2<br>AGT ACT ACT TAC<br>TAC TGG GTC | SEQ ID NO: 15<br>SISYSGSTYYNPSLKS<br>SEQ ID NO: 16<br>AGT ATC TCT TAT AGT<br>GGG AGC ACC TAC<br>TAC AAT CCG TCC CTC<br>AAG AGT | SEQ ID NO: 5<br>HLGYNGRYLPFDY<br>SEQ ID NO: 6<br>CAT CTA GGG TAT AAT<br>GGG AGG TAC CTC CCC<br>TTT GAC TAC |
| 1.103.11<br>hAb -<br>VH(20975-<br>VL) | SEQ ID NO: 7<br>TGTSSDVGFYNYVS<br>SEQ ID NO: 8<br>ACT GGA ACC AGC<br>AGT GAC GTT GGT<br>TTT TAT AAC TAT<br>GTC TCC | SEQ ID NO: 17<br>DVSNRPS<br>SEQ ID NO: 18<br>GAT GTC AGT AAT<br>CGG CCC TCA | SEQ ID NO: 19<br>SSYTNISTWV<br>SEQ ID NO: 20<br>AGC TCA TAT ACA AAC<br>ATC AGC ACT TGG GTG |
| 1.139.15<br>hAb -<br>VH(23521-<br>VH) | SEQ ID NO: 21<br>STTYYWG<br>SEQ ID NO: 22<br>AGT ACT ACT TAC<br>TAC TGG GGC | SEQ ID NO: 23<br>SISYSGTTYYNPSLKS<br>SEQ ID NO: 24<br>AGT ATC TCT TAT AGT<br>GGG ACC ACC TAC<br>TAC AAC CCG TCC CTC<br>AAG AGT | SEQ ID NO: 25<br>HLGYNSNWYPFDY<br>SEQ ID NO: 26<br>CAT CTC GGG TAT AAC<br>AGC AAC TGG TAC CCT<br>TTT GAC TAC |
| 1.139.15<br>hAb -<br>VH(23521-<br>VL) | SEQ ID NO: 27<br>TGTSSDVGSYNRVS<br>SEQ ID NO: 28<br>ACT GGA ACC AGC<br>AGT GAC GTT GGT<br>AGT TAT AAC CGT<br>GTC TCC | SEQ ID NO: 29<br>EVSNRPS<br>SEQ ID NO: 30<br>GAG GTC AGT AAT<br>CGG CCC TCA | SEQ ID NO: 31<br>SSYTSSSTWV<br>SEQ ID NO: 32<br>AGC TCA TAT ACA AGC<br>AGC AGC ACT TGG GTG |
| 1.153.7<br>hAb -<br>VH(20942-<br>VH) | SEQ ID NO: 33<br>SHAMS<br>SEQ ID NO: 34<br>AGC CAT GCC ATG<br>AGC | SEQ ID NO: 35<br>TITGGGGSIYYADSVKG<br>SEQ ID NO: 36<br>ACT ATT ACT GGT GGT<br>GGT GGT AGC ATA<br>TAC TAC GCA GAC TCC<br>GTG AAG GGC | SEQ ID NO: 37<br>NRAGEGYFDY<br>SEQ ID NO: 38<br>AAC CGC GCT GGG<br>GAG GGT TAC TTT GAC<br>TAC |
| 1.153.7<br>hAb -<br>VH(20942-<br>VL) | SEQ ID NO: 39<br>GGDNIGNKDVH<br>SEQ ID NO: 40<br>GGG GGA GAC AAC<br>ATT GGA AAT AAA<br>GAT GTG CAC | SEQ ID NO: 41<br>RDSNRPS<br>SEQ ID NO: 42<br>AGG GAT AGC AAC<br>CGG CCC TCT | SEQ ID NO: 43<br>QVWDSIWV<br>SEQ ID NO: 44<br>CAG GTG TGG GAC AGC<br>ATT TGG GTG |
| 1.103.11-v2<br>hAb -<br>VH(20975-<br>VH) | SEQ ID NO: 1<br>STTYYWV<br>SEQ ID NO: 2<br>AGT ACT ACT TAC<br>TAC TGG GTC | SEQ ID NO: 15<br>SISYSGSTYYNPSLKS<br>SEQ ID NO: 16<br>AGT ATC TCT TAT AGT<br>GGG AGC ACC TAC<br>TAC AAT CCG TCC CTC<br>AAG AGT | SEQ ID NO: 5<br>HLGYNGRYLPFDY<br>SEQ ID NO: 6<br>CAT CTA GGG TAT AAT<br>GGG AGG TAC CTC CCC<br>TTT GAC TAC |
| 1.103.11-v2<br>hAb -<br>VH(20975-<br>2-VL) | SEQ ID NO: 7<br>TGTSSDVGFYNYVS<br>SEQ ID NO: 8<br>ACT GGA ACC AGC<br>AGT GAC GTT GGT<br>TTT TAT AAC TAT<br>GTC TCC | SEQ ID NO: 17<br>DVSNRPS<br>SEQ ID NO: 18<br>GAT GTC AGT AAT<br>CGG CCC TCA | SEQ ID NO: 65<br>SSYTSISTWV<br>SEQ ID NO: 66<br>AGC TCA TAT ACA AGC<br>ATC AGC ACT TGG GTG |

1.7.3 hAb-VH(23466-VH): (SEQ ID NO:45 for amino acid and SEQ ID NO:46 for nucleic acid) with heavy chain CDRs1-3: SEQ TD NOs: 1, 3, 5 are amino acid sequences and SEQ ID NO:2, 4, 6 are nucleic acid sequences, respectively:

```
V segment: IGHV4-39*01
D segment: IGHD1-26*01
J segment: IGHJ4*02
      Q    L    Q    L    Q    E    S    G    P    G    L    V    K    P    S
1    CAG  CTG  CAG  CTG  CAG  GAG  TCG  GGC  CCA  GGA  CTG  GTG  AAG  CCT  TCG
      E    T    L    T    L    T    C    T    V    S    G    D    S    I    S
46   GAG  ACC  CTG  ACC  CTC  ACC  TGC  ACC  GTC  TCT  GGT  GAC  TCC  ATC  AGC
                              CDR1
                     ~~~~~~~~~~~~~~~~~~~~~~~~~~~~~~

S    T    T    Y    Y    W    V    W    I    R    Q    P    P    G    K
91   AGT  ACT  ACT  TAC  TAC  TGG  GTC  TGG  ATC  CGC  CAG  CCC  CCA  GGG  AAG
                                                       CDR2
                                                  ~~~~~~~~~~~~~~~~~~~~~~~~~~~~~

G    L    E    W    I    G    S    I    S    Y    S    G    N    T    Y
136  GGA  CTG  GAG  TGG  ATT  GGG  AGT  ATC  TCT  TAT  AGT  GGG  AAC  ACC  TAC
                     CDR2
           ~~~~~~~~~~~~~~~~~~~~~~~~~~~~~~~

Y    N    P    S    L    K    S    R    V    T    I    S    V    D    T
181  TAC  AAT  CCG  TCC  CTC  AAG  AGT  CGA  GTC  ACC  ATA  TCC  GTA  GAC  ACG
      S    K    N    H    F    S    L    K    L    S    S    V    A    A    T
226  TCC  AAG  AAC  CAC  TTC  TCC  CTG  AAG  CTG  AGT  TCT  GTC  GCC  GCC  ACA
                                                            CDR3
                                                  ~~~~~~~~~~~~~~~~~~~~~~~~~~~~~

D    T    A    L    Y    Y    C    A    R    H    L    G    Y    N    G
271  GAC  ACG  GCT  CTA  TAT  TAC  TGT  GCG  AGA  CAT  CTA  GGG  TAT  AAT  GGG
                     CDR3
           ~~~~~~~~~~~~~~~~~~~~~~~~~~~~~~~

R    Y    L    P    F    D    Y    W    G    Q    G    T    L    V    T
316  AGG  TAC  CTC  CCC  TTT  GAC  TAC  TGG  GGC  CAG  GGA  ACC  CTG  GTC  ACC
      V    S    S   (SEQ ID NO: 45)
361  GTC  TCC  TCC (SEQ ID NO: 46)
```

1.7.3 hAb-VL(23195-VL): (SEQ ID NO:47 for amino acid and SEQ ID NO:48 for nucleic acid) with light chain CDRs1-3: SEQ ID NOs: 7, 9, 11 are amino acid sequences and SEQ ID NO:8, 10, 12 are nucleic acid sequences, respectively:

```
V segment: IGLV2-14*01
J segment: IGLJ3*02

Q    S    A    L    T    Q    P    A    S    V    S    G    S    P    G
1    CAG  TCT  GCC  CTG  ACT  CAG  CCT  GCC  TCC  GTG  TCT  GGG  TCT  CCT  GGA
                                                       CDR1
                                        ~~~~~~~~~~~~~~~~~~~~~~~~~~~~~~~~~~~~~~~~

Q    S    I    T    I    S    C    T    G    T    S    S    D    V    G
46   CAG  TCG  ATC  ACC  ATC  TCC  TGC  ACT  GGA  ACC  AGC  AGT  GAC  GTT  GGT
                     CDR1
           ~~~~~~~~~~~~~~~~~~~~~~~~~~~~~~

F    Y    N    Y    V    S    W    Y    Q    Q    H    P    G    K    A
91   TTT  TAT  AAC  TAT  GTC  TCC  TGG  TAC  CAA  CAG  CAC  CCA  GGC  AAA  GCC
                                                  CDR2
                                        ~~~~~~~~~~~~~~~~~~~~~~~~~~~~~~~~~

P    E    L    M    I    Y    D    V    T    N    R    P    S    G    V
136  CCC  GAA  CTC  ATG  ATT  TAT  GAT  GTC  ACT  AAT  CGG  CCC  TCA  GGG  GTT

S    D    R    F    S    G    S    K    S    G    N    T    A    S    L
181  TCT  GAT  CGC  TTC  TCT  GGC  TCC  AAG  TCT  GGC  AAC  ACG  GCC  TCC  CTG

T    I    S    G    L    Q    A    E    D    E    A    D    Y    Y    C
226  ACC  ATC  TCT  GGG  CTC  CAG  GCT  GAG  GAC  GAG  GCT  GAT  TAT  TAC  TGC
```

40

-continued

```
                                    CDR3
       ‿‿‿‿‿‿‿‿‿‿‿‿‿‿‿‿‿‿‿‿‿‿‿‿‿‿‿‿‿‿‿‿‿‿
       S   S   Y   T   S   I   S   T   W   V   F   G   G   G   T
  261 AGC TCA TAT ACA AGC ATC AGC ACT TGG GTG TTC GGC GGA GGG ACC
       K   L   T   V   L   (SEQ ID NO: 47)
  316 AAG CTG ACC GTC CTA (SEQ ID NO: 48)
```

1.49.9 hAb-VH(20951-VH): (SEQ ID NO:49 for amino acid and SEQ ID NO:50 for nucleic acid) with heavy chain CDRs 1-3: SEQ ID NOs: 13, 15, 5 are amino acid sequences and SEQ ID NO:14, 16, 6 are nucleic acid sequences, respectively:

```
V segment: IGHV4-39*01
D segment: IGHD1-26*01
J segment: IGHJ4*02
       Q   L   Q   L   Q   E   S   G   P   G   L   V   K   P   S
    1 CAG CTG CAG CTG CAG GAG TCG GGC CCA GGA CTG GTG AAG CCT TCG
       E   T   L   S   L   T   C   T   V   S   G   g   S   I   S
   46 GAG ACC CTG TCC CTC ACC TGC ACT GTC TCT GGT GGC TCC ATC AGC
                          CDR1
           ‿‿‿‿‿‿‿‿‿‿‿‿‿‿‿‿‿‿‿‿‿‿‿‿‿‿‿‿
       S   S   T   Y   Y   W   G   W   I   R   Q   P   P   G   K
   91 AGT AGT ACT TAC TAC TGG GGC TGG ATC CGC CAG CCC CCA GGG AAG
                                          CDR2
                              ‿‿‿‿‿‿‿‿‿‿‿‿‿‿‿‿‿‿‿‿‿‿‿‿‿‿‿‿
       G   L   E   W   I   G   S   I   S   Y   S   G   S   T   Y
  136 GGA CTG GAG TGG ATT GGG AGT ATC TCT TAT AGT GGG AGC ACC TAC
                  CDR2
       ‿‿‿‿‿‿‿‿‿‿‿‿‿‿‿‿‿‿‿‿‿‿‿‿
       Y   N   P   S   L   K   S   R   V   T   I   S   V   D   T
  181 TAC AAT CCG TCC CTC AAG AGT CGA GTC ACC ATA TCC GTA GAC ACG
       S   K   N   Q   F   S   L   K   L   S   S   V   T   D   T
  226 TCC AAG AAC CAG TTC TCC CTG AAG CTG AGC TCT GTG ACC GAC ACG
                                          CDR3
                              ‿‿‿‿‿‿‿‿‿‿‿‿‿‿‿‿‿‿‿‿‿‿‿‿‿‿‿‿
       D   T   A   V   Y   Y   C   A   R   H   L   G   Y   N   G
  261 GAC ACG GCT GTG TAT TAC TGT GCG AGA CAT CTA GGG TAT AAT GGG
                  CDR3
       ‿‿‿‿‿‿‿‿‿‿‿‿‿‿‿‿‿‿‿‿‿‿‿‿
       R   Y   L   P   F   D   Y   W   G   Q   G   T   L   V   T
  316 AGG TAC CTC CCC TTT GAC TAC TGG GGC CAG GGA ACC CTG GTC ACC
       V   S   S   (SEQ ID NO: 49)
  361 GTC TCC TCC (SEQ ID NO: 50)
```

1.49.9 hAb-VL(21526-VL): (SEQ ID NO:51 for amino acid and SEQ ID NO:52 for nucleic acid) with light chain CDRs 1-3: SEQ ID NOs: 7, 17, 11 are amino acid sequences and SEQ ID NO:8, 18, 12 are nucleic acid sequences, respectively:

```
V segment: IGLV2-14*01
J segment: IGLJ3*02
       Q   S   A   L   T   Q   P   A   S   V   S   G   S   P   G
    1 CAG TCT GCC CTG ACT CAG CCT GCC TCC GTG TCT GGG TCT CCT GGA
                                          CDR1
                              ‿‿‿‿‿‿‿‿‿‿‿‿‿‿‿‿‿‿‿‿‿‿‿‿‿‿‿‿
       Q   S   I   T   I   S   C   T   G   T   S   S   D   V   G
   46 CAG TCG ATC ACC ATC TCC TGC ACT GGA ACC AGC AGT GAC GTT GGT
                  CDR1
       ‿‿‿‿‿‿‿‿‿‿‿‿‿‿‿‿‿‿‿‿‿‿‿‿
       F   Y   N   Y   V   S   W   Y   Q   Q   H   P   G   K   A
   91 TTT TAT AAC TAT GTC TCC TGG TAC CAA CAG CAC CCA GGC AAA GCC
```

-continued

```
                                                            CDR2
                                         ‿‿‿‿‿‿‿‿‿‿‿‿‿‿‿‿‿‿‿‿‿‿‿‿‿‿‿‿‿‿‿‿‿‿
        P    E    V    M    I    Y    D    V    S    N    R    P    S    G    V
136   CCC  GAA  GTC  ATG  ATT  TAT  GAT  GTC  AGT  AAT  CGG  CCC  TCA  GGG  GTT

S    D    R    F    S    G    S    K    S    G    N    T    A    S    L
181   TCT  GAT  CGC  TTC  TCT  GGC  TCC  AAG  TCT  GGC  AAC  ACG  GCC  TCC  CTG

T    I    S    G    L    Q    A    E    D    E    A    D    Y    Y    C
226   ACC  ATC  TCT  GGG  CTC  CAG  GCT  GAG  GAC  GAG  GCT  GAT  TAT  TAC  TGC

CDR3
      ‿‿‿‿‿‿‿‿‿‿‿‿‿‿‿‿‿‿‿‿‿‿‿‿‿‿‿‿‿‿‿‿‿‿‿‿‿‿‿‿‿‿‿‿‿‿‿‿

S    S    Y    T    S    I    S    T    W    V    F    G    G    G    T
261   AGC  TCA  TAT  ACA  AGC  ATC  AGC  ACT  TGG  GTG  TTC  GGC  GGA  GGG  ACC

K    L    T    V    L    (SEQ ID NO: 51)
316   AAG  CTG  ACT  GTC  CTA  (SEQ ID NO: 52)
```

1.103.11 hAb-VH(20975-VH): (SEQ ID NO:53 for amino acid and SEQ ID NO:54 for nucleic acid) with heavy chain CDRs 1-3: SEQ ID NOs: 1, 15, 5 are amino acid sequences and SEQ ID NO:2, 16, 6 are nucleic acid sequences, respectively:

```
V segment: IGHV4-39*01
D segment: IGHD1-26*01
J segment: IGHJ4*02

Q    L    Q    L    Q    E    S    G    P    G    L    V    K    P    S
1     CAG  CTG  CAG  CTG  CAG  GAG  TCG  GGC  CCA  GGA  CTG  GTG  AAG  CCT  TCG

E    T    L    T    L    T    C    T    V    S    A    D    S    I    S
46    GAG  ACC  CTG  ACC  CTC  ACC  TGC  ACT  GTC  TCT  GCT  GAC  TCC  ATC  AGC

CDR1
      ‿‿‿‿‿‿‿‿‿‿‿‿‿‿‿‿‿‿‿‿‿‿‿‿‿‿‿‿‿‿‿‿‿‿‿‿

S    T    T    Y    Y    W    V    W    I    R    Q    P    P    G    K
91    AGT  ACT  ACT  TAC  TAC  TGG  GTC  TGG  ATC  CGC  CAG  CCC  CCA  GGG  AAG

CDR2
                                         ‿‿‿‿‿‿‿‿‿‿‿‿‿‿‿‿‿‿‿‿‿‿‿‿‿‿‿‿‿‿‿‿‿‿
        G    L    E    W    I    G    S    I    S    Y    S    G    S    T    Y
136   GGA  CTG  GAG  TGG  ATT  GGG  AGT  ATC  TCT  TAT  AGT  GGG  AGC  ACC  TAC

CDR2
      ‿‿‿‿‿‿‿‿‿‿‿‿‿‿‿‿‿‿‿‿‿‿‿‿‿‿‿‿‿‿‿‿‿‿‿
        Y    N    P    S    L    K    S    R    V    T    V    S    V    D    T
181   TAC  AAT  CCG  TCC  CTC  AAG  AGT  CGA  GTC  ACC  GTA  TCC  GTA  GAC  ACG

S    K    N    Q    F    S    L    K    L    N    S    V    A    A    T
226   TCC  AAG  AAC  CAG  TTC  TCC  CTG  AAG  CTG  AAC  TCT  GTG  GCC  GCC  ACA

CDR3
                                         ‿‿‿‿‿‿‿‿‿‿‿‿‿‿‿‿‿‿‿‿‿‿‿‿‿‿‿‿‿‿‿‿‿‿
        D    T    A    L    Y    Y    C    A    R    H    L    G    Y    N    G
261   GAC  ACG  GCT  CTA  TAT  TAC  TGT  GCG  AGA  CAT  CTA  GGG  TAT  AAT  GGG

CDR3
      ‿‿‿‿‿‿‿‿‿‿‿‿‿‿‿‿‿‿‿‿‿‿‿‿‿‿‿‿‿‿‿‿‿‿‿
        R    Y    L    P    F    D    Y    W    G    Q    G    T    L    V    T
316   AGG  TAC  CTC  CCC  TTT  GAC  TAC  TGG  GGC  CAG  GGA  ACC  CTG  GTC  ACC

V    S    S    (SEQ ID NO: 53)
361   GTC  TCC  TCC  (SEQ ID NO: 54)
```

1.103.11 hAb-VL(21038-VL): (SEQ ID NO:55 for amino acid and SEQ ID NO:56 for nucleic acid) with light chain CDRs 1-3: SEQ ID NOs: 7, 17, 19 are amino acid sequences and SEQ ID NO:8, 18, 20 are nucleic acid sequences, respectively:

```
V segment: IGLV2-14*01
J segment: IGLJ3*02

Q    S    A    L    T    Q    P    A    S    V    S    G    S    P    G
1     CAG  TCT  GCC  CTG  ACT  CAG  CCT  GCC  TCC  GTG  TCT  GGG  TCT  CCT  GGA
```

-continued

```
                                                      CDR1
                        ^^^^^^^^^^^^^^^^^^^^^^^^^^^^^^^^^^^^^^^^^^^^^^
       Q    S    I    T    I    S    C    T    G    T    S    S    D    V    G
46     CAG  TCG  ATC  ACC  ATC  TCC  TGC  ACT  GGA  ACC  AGC  AGT  GAC  GTT  GGT
              CDR1
        ^^^^^^^^^^^^^^^^^^^^^^^^^^^^^^
       F    Y    N    Y    V    S    W    Y    Q    Q    H    P    G    K    A
91     TTT  TAT  AAC  TAT  GTC  TCC  TGG  TAC  CAA  CAG  CAC  CCA  GGC  AAA  GCC
                                                      CDR2
                                               ^^^^^^^^^^^^^^^^^^^^^^^^^^^^^^^^^
       P    E    L    M    I    Y    D    V    S    N    R    P    S    G    V
136    CCC  GAA  CTC  ATG  ATT  TAT  GAT  GTC  AGT  AAT  CGG  CCC  TCA  GGG  GTT
       S    D    R    F    S    G    S    K    S    G    N    T    A    S    L
181    TCT  GAT  CGC  TTC  TCT  GGC  TCC  AAG  TCT  GGC  AAC  ACG  GCC  TCC  CTG
       T    I    S    G    L    Q    A    E    D    E    A    D    Y    Y    C
226    ACC  ATC  TCT  GGG  CTC  CAG  GCT  GAG  GAC  GAG  GCT  GAT  TAT  TAC  TGC
                 CDR3
        ^^^^^^^^^^^^^^^^^^^^^^^^^^^^^^^^^^^^^^^^^^^^^^^^^
       S    S    Y    T    N    I    S    T    W    V    F    G    G    G    T
261    AGC  TCA  TAT  ACA  AAC  ATC  AGC  ACT  TGG  GTG  TTC  GGC  GGA  GGG  ACC
       K    L    T    V    L    (SEQ ID NO: 55)
316    AAG  CTG  ACC  GTC  CTA  (SEQ ID NO: 56)
```

1.139.15 hAb-VH(23521-VH) (SEQ ID NO:57 for amino
acid and SEQ ID NO:58 for nucleic acid) with heavy
chain CDRs 1-3: SEQ ID NOs: 21, 23, 25 are amino
acid sequences and SEQ ID NO:22, 24, 26 are nucleic
acid sequences, respectively:

```
V segment: IGHV4-39*01
D segment: IGHD6-13*01
J segment: IGHJ4*02
       Q    L    Q    L    Q    E    S    G    P    G    L    V    K    P    S
1      CAG  CTG  CAG  CTG  CAG  GAG  TCG  GGC  CCA  GGA  CTG  GTG  AAG  CCC  TCG
       E    T    L    S    L    T    C    T    V    S    G    G    S    I    S
46     GAG  ACC  CTG  TCC  CTC  ACC  TGC  ACT  GTC  TCT  GGT  GGC  TCC  ATC  AGC
                        CDR1
        ^^^^^^^^^^^^^^^^^^^^^^^^^^^^^^^^^^^
       S    T    T    Y    Y    W    G    W    I    R    Q    P    P    G    K
91     AGT  ACT  ACT  TAC  TAC  TGG  GGC  TGG  ATC  CGC  CAG  CCC  CCA  GGG  AAG
                                                      CDR2
                                          ^^^^^^^^^^^^^^^^^^^^^^^^^^^^^^^^^^^^
       G    L    E    W    I    G    S    I    S    Y    S    G    T    T    Y
136    GGG  CTG  GAG  TGG  ATT  GGG  AGT  ATC  TCT  TAT  AGT  GGG  ACC  ACC  TAC
              CDR2
        ^^^^^^^^^^^^^^^^^^^^^^^^^^^^^^^^^^^
       Y    N    P    S    L    K    S    R    V    T    I    P    V    D    T
181    TAC  AAC  CCG  TCC  CTC  AAG  AGT  CGA  GTC  ACC  ATC  CCC  GTA  GAC  ACG
       S    K    N    Q    I    S    L    K    L    S    S    V    T    A    A
226    TCC  AAG  AAC  CAG  ATC  TCC  CTG  AAA  CTG  AGC  TCT  GTG  ACC  GCC  GCA
                                                           CDR3
                                               ^^^^^^^^^^^^^^^^^^^^^^^^^^^^^^^^^
       D    T    S    L    Y    Y    C    A    R    H    L    G    Y    N    S
261    GAC  ACG  TCT  TTG  TAT  TAT  TGT  GCG  AGA  CAT  CTC  GGG  TAT  AAC  AGC
              CDR3
        ^^^^^^^^^^^^^^^^^^^^^^^^^^^^^^^^^^^
       N    W    Y    P    F    D    Y    W    G    Q    G    T    L    V    T
316    AAC  TGG  TAC  CCT  TTT  GAC  TAC  TGG  GGC  CAG  GGA  ACC  CTG  GTC  ACC
       V    S    S    (SEQ ID NO: 57)
361    GTC  TCC  TCA  (SEQ ID NO: 58)
```

1.139.15 hAb-VL(22895-VL) (SEQ ID NO:59 for amino
acid and SEQ ID NO:60 for nucleic acid) with light
chain CDRs 1-3: SEQ ID NOs: 27, 29, 31 are amino
acid sequences and SEQ ID NO: 28, 30, 32 are nucleic
acid sequences, respectively:

V segment: IGLV2-18*02
J segment: IGLJ3*02

```
     Q    S    A    L    T    Q    P    P    S    V    S    G    S    P    G
1    CAG  TCG  GCC  CTG  ACT  CAG  CCT  CCC  TCC  GTG  TCC  GGG  TCT  CCT  GGA
                                                                 CDR1
                                            ~~~~~~~~~~~~~~~~~~~~~~~~~~~~~~~~~~

Q    S    V    T    I    S    C    T    G    T    S    S    D    V    G
46   CAG  TCA  GTC  ACC  ATC  TCC  TGC  ACT  GGA  ACC  AGC  AGT  GAC  GTT  GGT
               CDR1
     ~~~~~~~~~~~~~~~~~~~~~~~~~~~~

S    Y    N    R    V    S    W    Y    Q    Q    P    P    G    T    A
91   AGT  TAT  AAC  CGT  GTC  TCC  TGG  TAC  CAG  CAG  CCC  CCA  GGC  ACA  GCC
                                                 CDR2
                                       ~~~~~~~~~~~~~~~~~~~~~~~~~~~~~~~~

P    E    V    I    I    Y    E    V    S    N    R    P    S    G    V
136  CCC  GAA  GTC  ATT  ATT  TAT  GAG  GTC  AGT  AAT  CGG  CCC  TCA  GGG  GTC
     P    D    R    F    S    G    S    K    S    G    N    T    A    S    L
181  CCT  GAT  CGC  TTC  TCT  GGG  TCC  AAG  TCT  GGC  AAC  ACG  GCC  TCC  CTG
     T    I    S    G    L    Q    A    E    D    E    A    D    Y    Y    C
226  ACC  ATC  TCT  GGG  CTC  CAG  GCT  GAG  GAC  GAG  GCT  GAT  TAT  TAC  TGC
                    CDR3
     ~~~~~~~~~~~~~~~~~~~~~~~~~~~~~~~~~~~~~~~~~~~~~~~~~~~~~~~~~~~

S    S    Y    T    S    S    S    T    W    V    F    G    G    G    T
261  AGC  TCA  TAT  ACA  AGC  AGC  AGC  ACT  TGG  GTG  TTC  GGC  GGA  GGG  ACC
     K    L    T    V    L   (SEQ ID NO: 59)
316  AAG  CTG  ACC  GTC  CTA (SEQ ID NO: 60)
```

1.153.7 hAb-VH(20942-VH): (SEQ ID NO:61 for amino acid and SEQ ID NO:62 for nucleic acid) with heavy 30 chain CDRs 1-3: SEQ ID NOs: 33, 35, 37 are amino acid sequences and SEQ ID NO: 34, 36, 38 are nucleic acid sequences, respectively:

V segment: IGHV3-23*01
D segment: IGHD7-27*01
J segment: IGHJ4*02

```
     E    V    Q    L    L    E    S    G    G    G    L    V    Q    P    G
1    GAG  GTG  CAG  CTG  TTG  GAG  TCT  GGG  GGA  GGC  TTG  GTA  CAG  CCT  GGG

G    S    L    R    L    S    C    A    A    S    G    F    T    F    S
46   GGG  TCC  CTG  AGA  CTG  TCC  TGC  GCA  GCC  TCT  GGA  TTC  ACC  TTT  AGC
                         CDR1
               ~~~~~~~~~~~~~~~~~~~~~~~~~

S    H    A    M    S    W    V    R    Q    A    P    G    K    G    L
91   AGC  CAT  GCC  ATG  AGC  TGG  GTC  CGC  CAG  GCT  CCA  GGG  AAG  GGG  CTG
                                                 CDR2
                                       ~~~~~~~~~~~~~~~~~~~~~~~~~~~~~~~~~~~~~~~~

E    W    V    S    T    I    T    G    G    G    G    S    I    Y    Y
136  GAG  TGG  GTC  TCA  ACT  ATT  ACT  GGT  GGT  GGT  GGT  AGC  ATA  TAC  TAC
                    CDR2
     ~~~~~~~~~~~~~~~~~~~~~~~~~~~~~~~~~~~~

A    D    S    V    K    G    R    F    T    I    S    R    D    N    S
181  GCA  GAC  TCC  GTG  AAG  GGC  CGG  TTC  ACC  ATC  TCC  AGA  GAC  AAT  TCC
     K    N    T    L    Y    L    Q    M    N    S    L    R    A    E    D
226  AAG  AAC  ACG  CTG  TAT  CTG  CAA  ATG  ACC  AGC  CTG  AGA  GCC  GAG  GAC
                                                           CDR3
                                            ~~~~~~~~~~~~~~~~~~~~~~~~~~~~~~~~~~~

T    A    V    Y    Y    C    A    K    N    R    A    G    E    G    Y
261  ACG  GCC  GTA  TAT  TAT  TGT  GCG  AAA  AAC  CGC  GCT  GGG  GAG  GGT  TAC
          CDR3
     ~~~~~~~~~~~~~~~~~~~~~

F    D    Y    W    G    Q    G    T    L    V    T    V    S    S   (SEQ ID NO: 61)
316  TTT  GAC  TAC  TGG  GGC  CAG  GGA  ACC  CTG  GTC  ACC  GTC  TCC  TCA (SEQ ID NO: 62)
```

1.153.7 hAb-VL(21110-VL) (SEQ ID NO:63 for amino
acid and SEQ ID NO:64 for nucleic acid) with light
chain CDRs 1-3: SEQ ID NOs: 39, 41, 43 are amino
acid sequences and SEQ ID NO: 40, 42, 44 are nucleic
acid sequences, respectively:

```
V segment: IGLV3-9*01
J segment: IGLJ3*02
      S    Y    E    L    T    Q    P    L    S    V    S    V    A    L    G
1     TCC  TAT  GAG  CTG  ACT  CAG  CCA  CTC  TCA  GTG  TCA  GTG  GCC  CTG  GGA
                                                                  CDR1
                                      ~~~~~~~~~~~~~~~~~~~~~~~~~~~~~~~~~~~~~~~

Q    T    A    R    I    T    C    G    G    D    N    I    G    N    K
46    CAG  ACG  GCC  AGG  ATT  ACC  TGT  GGG  GGA  GAC  AAC  ATT  GGA  AAT  AAA
           CDR1
      ~~~~~~~~~~~~

D    V    H    W    Y    Q    Q    K    P    G    Q    A    P    V    L
91    GAT  GTG  CAC  TGG  TAC  CAG  CAG  AAG  CCA  GGC  CAG  GCC  CCT  GTG  CTG
                                      CDR2
                          ~~~~~~~~~~~~~~~~~~~~~~~~~~~~~~~~~~~~

V    I    Y    R    D    S    N    R    P    S    G    I    P    E    G
136   GTC  ATC  TAT  AGG  GAT  AGC  AAC  CGG  CCC  TCT  GGG  ATC  CCT  GAG  GGA
      F    S    G    S    N    S    G    N    T    A    T    L    T    I    S
181   TTC  TCT  GGC  TCC  AAC  TCG  GGG  AAC  ACG  GCC  ACC  CTG  ACC  ATC  AGC
                                                                  CDR3
                                                        ~~~~~~~~~~~~~~~~~~~~~

R    A    Q    A    G    D    E    A    D    Y    Y    C    Q    V    W
226   AGA  GCC  CAA  GCC  GGG  GAT  GAG  GCT  GAC  TAT  TAC  TGT  CAG  GTG  TGG
                CDR3
      ~~~~~~~~~~~~~~~~~~~~~~~~~~~~~~~~~~~~

D    S    I    W    V    F    G    G    G    T    K    L    T    V    L    (SEQ ID NO: 63)
261   GAC  AGC  ATT  TGG  GTG  TTC  GGC  GGA  GGG  ACC  AAG  CTG  ACC  GTC  CTA  (SEQ ID NO: 64)
```

1.103.11-v2 hAb-VH(20975-VH): (SEQ ID NO:53 for
amino acid and SEQ ID NO:54 for nucleic acid) with  35
heavy chain CDRs 1-3: SEQ ID NOs: 1, 15, 5 are
amino acid sequences and SEQ ID NO:2, 16, 6 are
nucleic acid sequences, respectively:

```
V segment: IGHV4-39*01
D segment: IGHD1-26*01
J segment: IGHJ4*02

Q    L    Q    L    Q    E    S    G    P    G    L    V    K    P    S
1     CAG  CTG  CAG  CTG  CAG  GAG  TCG  GGC  CCA  GGA  CTG  GTG  AAG  CCT  TCG

E    T    L    T    L    T    C    T    V    S    A    D    S    I    S
46    GAG  ACC  CTG  ACC  CTC  ACC  TGC  ACC  GTC  TCT  GCT  GAC  TCC  ATC  AGC
                          CDR1
                ~~~~~~~~~~~~~~~~~~~~~~~~~~~~~~~~~~~~~~

S    T    T    Y    Y    W    V    W    I    R    Q    P    P    G    K
91    AGT  ACT  ACT  TAC  TAC  TGG  GTC  TGG  ATC  CGC  CAG  CCC  CCA  GGG  AAG
                                                        CDR2
                                            ~~~~~~~~~~~~~~~~~~~~~~~~~~~~~~~~~~

G    L    E    W    I    G    S    I    S    Y    S    G    S    T    Y
136   GGA  CTG  GAG  TGG  ATT  GGG  AGT  ATC  TCT  TAT  AGT  GGG  AGC  ACC  TAC
                CDR2
      ~~~~~~~~~~~~~~~~~~~~~~~~~~~~~~~~~~~~

Y    N    P    S    L    K    S    R    V    T    V    S    V    D    T
181   TAC  AAT  CCG  TCC  CTC  AAG  AGT  CGA  GTC  ACC  GTA  TCC  GTA  GAC  ACG
      S    K    N    Q    F    S    L    K    L    N    S    V    A    A    T
226   TCC  AAG  AAC  CAG  TTC  TCC  CTG  AAG  CTG  AAC  TCT  GTC  GCC  GCC  ACA
                                                                  CDR3
                                                        ~~~~~~~~~~~~~~~~~~~~~

D    T    A    L    Y    Y    C    A    R    H    L    G    Y    N    G
261   GAC  ACG  GCT  CTA  TAT  TAC  TGT  GCG  AGA  CAT  CTA  GGG  TAT  AAT  GGG
```

-continued

```
                        CDR3
        ‿‿‿‿‿‿‿‿‿‿‿‿‿‿‿‿‿‿‿‿‿‿‿‿‿‿‿‿‿‿‿‿
       R    Y    L    P    F    D    Y    W    G    Q    G    T    L    V    T
316   AGG  TAC  CTC  CCC  TTT  GAC  TAC  TGG  GGC  CAG  GGA  ACC  CTG  GTC  ACC

V    S    S   (SEQ ID NO:  53)
361   GTC  TCC  TCC (SEQ ID NO:  54)
```

1.103.11-v2 hAb-VL(21038-2-VL): (SEQ ID NO:67 for amino acid and SEQ ID NO:68 for nucleic acid) with light chain CDRs 1-3: SEQ ID NOs: 7, 17, 65 are amino acid sequences and SEQ ID NO:8, 18, 66 are nucleic acid sequences, respectively:

```
V segment: IGLV2-14*01
J segment: IGLJ3*02
       Q    S    A    L    T    Q    P    A    S    V    S    G    S    P    G
1     CAG  TCT  GCC  CTG  ACT  CAG  CCT  GCC  TCC  GTG  TCT  GGG  TCT  CCT  GGA
                                                          CDR1
                                             ‿‿‿‿‿‿‿‿‿‿‿‿‿‿‿‿‿‿‿‿‿‿‿‿‿‿‿‿‿‿‿
       Q    S    I    T    I    S    C    T    G    T    S    S    D    V    G
46    CAG  TCG  ATC  ACC  ATC  TCC  TGC  ACT  GGA  ACC  AGC  AGT  GAC  GTT  GGT
                 CDR1
        ‿‿‿‿‿‿‿‿‿‿‿‿‿‿‿‿‿‿‿‿‿‿‿‿‿
       F    Y    N    Y    V    S    W    Y    Q    Q    H    P    G    K    A
91    TTT  TAT  AAC  TAT  GTC  TCC  TGG  TAC  CAA  CAG  CAC  CCA  GGC  AAA  GCC
                                                  CDR2
                                   ‿‿‿‿‿‿‿‿‿‿‿‿‿‿‿‿‿‿‿‿‿‿‿‿‿‿‿‿‿‿‿
       P    E    L    M    I    Y    D    V    S    N    R    P    S    G    V
136   CCC  GAA  CTC  ATG  ATT  TAT  GAT  GTC  AGT  AAT  CGG  CCC  TCA  GGG  GTT
       S    D    R    F    S    G    S    K    S    G    N    T    A    S    L
181   TCT  GAT  CGC  TTC  TCT  GGC  TCC  AAG  TCT  GGC  AAC  ACG  GCC  TCC  CTG
       T    I    S    G    L    Q    A    E    D    E    A    D    Y    Y    C
226   ACC  ATC  TCT  GGG  CTC  CAG  GCT  GAG  GAC  GAG  GCT  GAT  TAT  TAC  TGC
                 CDR3
        ‿‿‿‿‿‿‿‿‿‿‿‿‿‿‿‿‿‿‿‿‿‿‿‿‿‿‿‿‿‿‿‿‿‿‿‿‿‿‿‿‿‿‿
       S    S    Y    T    S    I    S    T    W    V    F    G    G    G    T
261   AGC  TCA  TAT  ACA  AGC  ATC  AGC  ACT  TGG  GTG  TTC  GGC  GGA  GGG  ACC
       K    L    T    V    L   (SEQ ID NO:  67)
316   AAG  CTG  ACC  GTC  CTA (SEQ ID NO:  68)
```

In some embodiments, the anti-PD-1 antibodies and the antigen-binding fragments for use comprise a heavy chain CDR sequences selected from the group consisting of: SEQ ID NOs: 1, 3, 5, 13, 15, 21, 23, 25, 33, 35 and 37. In some embodiments, the anti-PD-1 antibodies and the antigen-binding fragments thereof comprise a light chain CDR sequences selected from the group consisting of: SEQ ID NOs: 7, 9, 11, 17, 19, 27, 29, 31, 39, 41, 43 and 65. In certain embodiments, one or more CDR sequences provided herein can be modified or changed such that the resulting antibody is improved over the parent antibody in one or more properties (such as improved antigen-binding, improved glycosylation pattern, reduced risk of glycosylation on a CDR residue, reduced deamination on a CDR residue, increased pharmacokinetic half-life, pH sensitivity, and compatibility to conjugation), and is otherwise comparable to the parent antibody (i.e. antibody having otherwise the same set of CDR sequences except for the above-mentioned modification or change), or at least substantially retains the antigen-binding property of the parent antibody.

In some embodiments, the anti-PD-1 antibodies and the antigen-binding fragments for use comprise a heavy chain variable region selected from the group consisting of: a heavy chain variable region comprising SEQ ID NO: 1, SEQ ID NO: 3, and/or SEQ ID NO: 5; a heavy chain variable region comprising SEQ ID NO: 13, SEQ ID NO: 15, and/or SEQ ID NO: 5; a heavy chain variable region comprising SEQ ID NO: 1, SEQ ID NO: 15, and/or SEQ ID NO: 5; a heavy chain variable region comprising SEQ ID NO: 21, SEQ ID NO: 23, and/or SEQ ID NO: 25; and a heavy chain variable region comprising SEQ ID NO: 33, SEQ ID NO: 35, and/or SEQ ID NO: 37.

In some embodiments, the anti-PD-1 antibodies and the antigen-binding fragments for use comprise a light chain variable region selected from the group consisting of: a light chain variable region comprising SEQ ID NO: 7, SEQ ID NO: 9, and/or SEQ ID NO: 11; a light chain variable region comprising SEQ ID NO: 7, SEQ ID NO: 17, and/or SEQ ID NO: 11; a light chain variable region comprising SEQ ID NO: 7, SEQ ID NO: 17, and/or SEQ ID NO: 19; a light chain variable region comprising SEQ ID NO: 27, SEQ ID NO: 29, and/or SEQ ID NO: 31; a light chain variable region comprising SEQ ID NO: 39, SEQ ID NO: 41, and/or SEQ ID NO: 43; and a light chain variable region comprising SEQ ID NO: 7, SEQ ID NO: 17, and/or SEQ ID NO: 65.

In some embodiments, the anti-PD-1 antibodies and the antigen-binding fragments for use comprise: a) a heavy chain variable region comprising SEQ ID NO: 1, SEQ ID NO: 3, and/or SEQ ID NO: 5; and a light chain variable region comprising SEQ ID NO: 7, SEQ ID NO: 9, and/or SEQ ID NO: 11; b) a heavy chain variable region comprising SEQ ID NO: 13, SEQ ID NO: 15, and/or SEQ ID NO: 5; and a light chain variable region comprising SEQ ID NO:

7, SEQ ID NO: 17, and/or SEQ ID NO: 11; c) a heavy chain variable region comprising SEQ ID NO: 1, SEQ ID NO: 15, and/or SEQ ID NO: 5; and a light chain variable region comprising SEQ ID NO: 7, SEQ ID NO: 17, and/or SEQ ID NO: 19; d) a heavy chain variable region comprising SEQ ID NO: 21, SEQ ID NO: 23, and/or SEQ ID NO: 25 and a light chain variable region comprising SEQ ID NO: 27, SEQ ID NO: 29, and/or SEQ ID NO: 31; e) a heavy chain variable region comprising SEQ ID NO: 33, SEQ ID NO: 35, and/or SEQ ID NO: 37; and a light chain variable region comprising SEQ ID NO: 39, SEQ ID NO: 41, and/or SEQ ID NO: 43; or f) a heavy chain variable region comprising SEQ ID NO: 1, SEQ ID NO: 15, and/or SEQ ID NO: 5; and a light chain variable region comprising SEQ ID NO: 7, SEQ ID NO: 17, and/or SEQ ID NO: 65.

A skilled artisan will understand that the CDR sequences provided in Table 1 can be modified to contain one or more substitutions of amino acids, so as to provide for an improved biological activity such as improved binding affinity to human PD-1. For example, a library of antibody variants (such as Fab or scFv variants) can be generated and expressed with phage display technology, and then screened for the binding affinity to human PD-1. For another example, computer software can be used to virtually simulate the binding of the antibodies to human PD-1, and identify the amino acid residues on the antibodies which form the binding interface. Such residues may be either avoided in the substitution so as to prevent reduction in binding affinity, or targeted for substitution to provide for a stronger binding. In certain embodiments, at least one (or all) of the substitution(s) in the CDR sequences is conservative substitution.

In certain embodiments, the antibodies and the antigen-binding fragments for use comprise one or more CDR sequences having at least 80% (e.g. at least 85%, 88%, 90%, 91%, 92%, 93%, 94%, 95%, 96%, 97%, 98%, 99%) sequence identity to that (or those) listed in Table 1, and in the meantime retain the binding affinity to human PD-1 at a level similar to or even higher than its parental antibody having substantially the same sequence except that the corresponding CDR sequence is in 100% sequence identity to that (or those) listed in Table 1.

In some embodiments, the fully human anti-PD-1 antibodies and the antigen-binding fragments for use comprise a heavy chain variable region selected from the group consisting of: SEQ ID NO: 45, SEQ ID NO: 49, SEQ ID NO: 53, SEQ ID NO: 57, SEQ ID NO: 61, and a homologous sequence thereof having at least 80% (e.g. at least 85%, 88%, 90%, 91%, 92%, 93%, 94%, 95%, 96%, 97%, 98%, 99%) sequence identity; and/or a light chain variable region selected from the group consisting of: SEQ ID NO: 47, SEQ ID NO: 51, SEQ ID NO: 55, SEQ ID NO: 59, SEQ ID NO: 63, SEQ ID NO: 67, and a homologous sequence thereof having at least 80% (e.g. at least 85%, 88%, 90%, 91%, 92%, 93%, 94%, 95%, 96%, 97%, 98%, 99%) sequence identity. Theses fully human antibodies retain the binding affinity to human PD-1, preferably at a level similar to one of the exemplary antibodies: 1.7.3 hAb, 1.49.9 hAb, 1.103.11 hAb, 1.103.11-v2 hAb, 1.139.15 hAb, and 1.153.7 hAb.

In some embodiments, the fully human anti-PD-1 antibodies and the antigen-binding fragments for use comprise: a) a heavy chain variable region comprising SEQ ID NO: 45; and a light chain variable region comprising SEQ ID NO: 47; b) a heavy chain variable region comprising SEQ ID NO: 49; and a light chain variable region comprising SEQ ID NO: 51; c) a heavy chain variable region comprising SEQ ID NO: 53; and a light chain variable region comprising SEQ ID NO: 55; d) a heavy chain variable region comprising SEQ ID NO: 57; and a light chain variable region comprising SEQ ID NO: 59; e) a heavy chain variable region comprising SEQ ID NO: 61; and a light chain variable region comprising SEQ ID NO: 63; or f) a heavy chain variable region comprising SEQ ID NO: 53; and a light chain variable region comprising SEQ ID NO: 67.

In some embodiments, the fully human anti-PD-1 antibodies and the antigen-binding fragments for use comprise a heavy chain variable region comprising SEQ ID NO: 53; and a light chain variable region comprising SEQ ID NO: 67.

In some embodiments, the fully human anti-PD-1 antibodies for use is Antibody 1.

In some embodiments, the anti-PD-1 antibodies or antigen-binding fragments thereof provided herein are fully human antibodies. In certain embodiments, the fully human antibodies are prepared using recombinant methods. For example, transgenic animal such as a mouse can be made to carry transgenes or transchromosomes of human immunoglobulin genes, and therefore capable of producing fully human antibodies after immunization with proper antigen such as human PD-1. Fully human antibodies can be isolated from such transgenic animal, or alternatively, can be made by hybridoma technology by fusing the spleen cells of the transgenic animal with an immortal cell line to generate hybridoma cells secreting the fully human antibodies. Exemplary transgenic animals include, without limitation, OmniRat, whose endogenous expression of rat immunoglobulin genes are inactivated and at the same time engineered to contain functional recombinant human immunoglobulin loci; OmniMouse, whose endogenous expression of mouse immunoglobulin genes are inactivated and at the same time engineered to contain recombinant human immunoglobulin loci having J-locus deletion and a C-kappa mutation; OmniFlic, which is a transgenic rat whose endogenous expression of rat immunoglobulin genes are inactivated and at the same time engineered to contain recombinant human immunoglobulin loci having a single common, rearranged VkJk light chain and functional heavy chain. Detailed information can be further found at: Osborn M. et al, Journal of Immunology, 2013, 190: 1481-90; Ma B. et al, Journal of Immunological Methods 400-401 (2013) 78-86; Geurts A. et al, Science, 2009, 325:433; U.S. Pat. No. 8,907,157; EP patent 2152880B1; EP patent 2336329B1, all of which are incorporated herein by reference to its entirety. Other suitable transgenic animals can also be used, for example, HuMab mice (see, for details, Lonberg, N. et al. Nature 368(6474): 856 859 (1994)), Xeno-Mouse (Mendez et al. Nat Genet., 1997, 15:146-156), TransChromo Mouse (Ishida et al. Cloning Stem Cells, 2002, 4:91-102) and VelocImmune Mouse (Murphy et al. Proc Natl Acad Sci USA, 2014, 111:5153-5158), Kymouse (Lee et al. Nat Biotechnol, 2014, 32:356-363), and transgenic rabbit (Flisikowska et al. PLoS One, 2011, 6:e21045).

B. Pharmaceutical Compositions and Formulations

The anti-PD-1 antibodies or the antigen-binding fragments thereof used in the methods of the present invention can be delivered directly or with one or more pharmaceutically acceptable carriers.

Pharmaceutical acceptable carriers may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In some embodiments, pharmaceutical compositions and formulations may include compositions suitable for intravenous use.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical)

routes. In some embodiments, the antibodies and antigen-binding fragments disclosed herein are administered intravenously.

In certain embodiments, unit-dose parenteral preparations are packaged in an ampoule, a vial or a syringe with a needle. All preparations for parenteral administration should be sterile and not pyretic, as is known and practiced in the art.

C. Methods of Treatment

Provided herein are methods of treating solid tumors comprising administering to a subject in need thereof a therapeutically effective amount of the anti-PD-1 antibodies or the antigen-binding fragments thereof described herein.

The therapeutically effective amount of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of tumor development. Dosages may be proportionally reduced or increased by one of ordinary skill in the art (e.g., physician or veterinarian) as indicated by these and other circumstances or requirements.

In some embodiments, a therapeutically effective amount of anti-PD-1 antibodies or the antigen-binding fragments described herein is at least 80 mg. In some embodiments, a therapeutically effective amount of anti-PD-1 antibodies or the antigen-binding fragments described herein is about 240 mg, 360 mg, 480 mg, or 720 mg. In some embodiments, a therapeutically effective amount of anti-PD-1 antibodies or the antigen-binding fragments described herein is about 240 mg. In some embodiments, a therapeutically effective amount of anti-PD-1 antibodies or the antigen-binding fragments described herein is about 360 mg. In some embodiments, a therapeutically effective amount of anti-PD-1 antibodies or the antigen-binding fragments described herein is about 480 mg. In some embodiments, a therapeutically effective amount of anti-PD-1 antibodies or the antigen-binding fragments described herein is about 720 mg.

The therapeutically effective amount may be administered at various time points (e.g. daily, twice a week, weekly, once every two weeks, etc). In some embodiments, the therapeutically effective amount is administered about every 2 weeks, about every 3 weeks, about every 4 weeks, or about every 5 weeks. In some embodiments, the therapeutically effective amount is administered every 2 weeks. In some embodiments, the therapeutically effective amount is administered every 3 weeks. In some embodiments, the therapeutically effective amount is administered every 4 weeks. In some embodiments, the therapeutically effective amount is administered every 5 weeks.

It is recognized that the administration dosage may change over the course of treatment. For example, in certain embodiments the initial administration dosage may be higher than subsequent administration dosages. In certain embodiments, the administration dosage may vary over the course of treatment depending on the reaction of the subject.

In some embodiments, the solid tumor is an advanced solid tumor. Non-limiting examples of advanced solid tumors include metastatic tumors, recurrent tumors, or tumors which have not responded to one or more previously administered cancer therapeutics.

In some embodiments the solid tumor is selected from the group consisting of non-small-cell lung cancer, head and neck cancer, kidney cancer, breast cancer, bowel cancer, prostate cancer, bladder cancer, ovarian cancer, primary peritoneal cancer, esophageal cancer, malignant melanoma.

In some embodiments the solid tumor is selected from the group consisting of non-small-cell lung cancer, squamous cell carcinoma of the head and neck, renal cell carcinoma, breast cancer, colorectal cancer, prostate cancer, melanoma, bladder cancer, ovarian cancer, endometrial cancer, Merkel cell carcinoma, or gastroesophageal cancer.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes. In some embodiments, the antibodies and antigen-binding fragments disclosed herein are administered as a bolus or intravenously. In some embodiments, the antibodies and antigen-binding fragments disclosed herein are administered as an intravenous infusion over a period of about 2 hours. In some embodiments, the antibodies and antigen-binding fragments disclosed herein are administered as an intravenous infusion over a period of about 1 hour. In some embodiments, the antibodies and antigen-binding fragments disclosed herein are administered as an intravenous infusion over a period of about 30 minutes. In some embodiments, the antibodies and antigen-binding fragments disclosed herein are administered as an intravenous infusion over a period of less than 30 minutes.

The antibodies or antigen-binding fragments disclosed herein may be administered alone or in combination with one or more additional therapeutic means or agents. For example, the antibodies or antigen-binding fragments disclosed herein may be administered in combination with chemotherapy, radiation therapy, surgery for the treatment of cancer (e.g., tumorectomy), one or more anti-emetics or other treatments for complications arising from chemotherapy, or any other therapeutic agent for use in the treatment of cancer or any medical disorder mediated by PD-1. In certain of these embodiments, an antibody or antigen-binding fragment as disclosed herein that is administered in combination with one or more additional therapeutic agents may be administered simultaneously with the one or more additional therapeutic agents, and in certain of these embodiments the antibody or antigen-binding fragment and the additional therapeutic agent(s) may be administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

In certain embodiments, the therapeutic agents can induce or boost immune response against cancer. For example, a tumor vaccine can be used to induce immune response to certain tumor or cancer. Cytokine therapy can also be used to enhance tumor antigen presentation to the immune system. Examples of cytokine therapy include, without limitation, interferons such as interferon-α, -β, and -γ, colony stimulating factors such as macrophage-CSF, granulocyte macrophage CSF, and granulocyte-CSF, interleukins such IL-1, IL-1α, IL-2, IL-3, IL-4, IL-5, IL-6, IL-7, IL-8, IL-9, IL-10, IL-11, and IL-12, tumor necrosis factors such as TNF-α and TNF-β. Agents that inactivate immunosuppressive targets can also be used, for example, TGF-beta inhibitors, IL-10 inhibitors, and Fas ligand inhibitors. Another group of agents include those that activate immune responsiveness to tumor or cancer cells, for example, those enhance T cell activation (e.g. agonist of T cell costimulatory molecules such as CTLA-4, ICOS and OX-40), and those enhance dendritic cell function and antigen presentation.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

III. Examples

Example 1: Study to Evaluate the Safety and Tolerability of Antibody 1 in Subjects with Advanced Solid Tumors

1. Introduction

PD-1 is an inhibitory immune checkpoint protein that is expressed on activated B cells, T cells, and myeloid cells (Okazaki et al, 2001; Bennett et al, 2003), and it plays a key role in limiting the activity of effector T cells. It also provides a major resistance mechanism by which tumor cells can escape immune surveillance. When activated by its ligands, PD-1 induces a state of anergy or unresponsiveness in T cells, and the cells are unable to produce optimal levels of effector cytokines or carry out other effector T-cell functions. PD-1 may also induce apoptosis in T cells via its ability to inhibit survival signals. Under normal circumstances, PD-1 is important for limiting the extent of T-cell-mediated immune responses. PD-1-deficient animals develop various autoimmune phenotypes, including autoimmune cardiomyopathy and a lupus-like syndrome with arthritis and nephritis (Nishimura et al, 1999; Nishimura et al, 2001).

The interaction of PD-1 expressed on activated T cells and PD-L1 expressed on tumor cells negatively regulates immune response and dampens antitumor immunity. PD-L1 is abundantly expressed on a variety of human tumors (Dong et al, 2002), and its expression correlates with reduced patient survival in esophageal, pancreatic, and other types of cancers. Therefore, the PD-1/PD-L1 pathway is an important target for tumor immunotherapy. Activation of the PD-1/PD-L1 signaling pathway results in a decrease in tumor-infiltrating lymphocytes, a decrease in T-cell proliferation, and an increase in immune evasion by cancerous cells (Dong and Chen, 2003; Blank et al, 2005; Konishi et al, 2004). Immune suppression can be reversed by inhibiting the local interaction of PD-1 with PD-L1, and the effect is additive when the interaction of PD-1 with PD-L2 is also blocked.

2. Study Design

2.1. Overview

This example describes a Phase 1 open-label, dose-escalation study to evaluate the safety, tolerability, pharmacokinetic (PK), pharmacodynamic (PD), and clinical activity of Antibody 1 in subjects with select advanced solid tumors who have received up to 5 lines of prior therapies.

The study consists of 2 parts:

Part 1 (dose escalation) assesses increasing dose levels of Antibody 1 (80, 240, and 720 mg every 2 weeks [Q2W]) based on a 3+3 design, including dose-limiting toxicity (DLT) evaluation period. Intermediate Q2W doses and other schedules may also be explored. De-escalation to 80 mg every 3 weeks (Q3W) is permitted.

Part 2 (PK/PD confirmation) further evaluates Antibody 1 in 3 to 6 subjects per dosing schedule (for a total of up to 18 subjects) to confirm the PK/PD reported during Part 1. Part 2 may occur concurrent with Part 1; however, doses explored in Part 2 must not be higher than those being evaluated in Part 1, unless they have been cleared in Part 1 (eg, if 240 mg Q2W is cleared in Part 1, 360 mg Q3W and/or 480 mg every 4 weeks [Q4W] may be evaluated in Part 2). Safety will be evaluated on an ongoing basis.

A study design schema is provided in FIG. 1.

2.2. Pharmacokinetic Evaluation

Blood samples for analysis of Antibody 1 PK will be collected at the following timepoints:

For Q2W and Q4W dosing schedules: on days 1 (pre- and 1 hr post-dose), 2 (24 hrs post-dose), 3 (48 hrs post-dose), 8 (168 hrs post-dose), 15 (pre-dose), 29 (pre- and 1 hr post-dose), 43 (pre-dose), 57 (pre-dose) and 85 (pre-dose) of treatment, at end of treatment and 90 days post last dose;

For Q2W dosing schedule: on days 1 (pre- and 1 hr post-dose), 2 (24 hrs post-dose), 3 (48 hrs post-dose), 8 (168 hrs post-dose), 22 (pre- and 1 hr post-dose), 43 (pre- and 1 hr post-dose) and 64 (pre- and 1 hr post-dose) of treatment, at end of treatment and 90 days post last dose.

PK parameters, including but not limited to area under the concentration-time curve, $C_{max}$, and time to $C_{max}$, will be estimated using standard non-compartmental methods.

2.3. Immunogenicity Evaluation

Serum samples for immunogenicity analysis will be collected at the following timepoints:

For Q2W dosing schedule: on days 1, 15, 29, 43 and 85 of treatment, at end of treatment, 90 days post last dose and 6 months from end of treatment;

For Q3W dosing schedule: on days 1, 22 and 64 of treatment, at end of treatment, 90 days post last dose and 6 months from end of treatment;

For Q4W dosing schedule: on days 1, 29 and 85 of treatment, and end of treatment, 90 days post last dose and 6 months from end of treatment.

2.4. Pharmacodynamic Assessment

Whole blood samples will be collected for PD/receptor occupancy analysis at the following timepoints:

For Q2W dosing schedule: on days 1 (pre- and 1 hr post-dose), 2 (24 hrs post-dose), 15 (pre-dose), 29 (pre-dose), 57 (pre-dose) and 85 (pre-dose) of treatment, at end of treatment and 90 days post last dose;

For Q3W dosing schedule: on days 1 (pre- and 1 hr post-dose), 2 (24 hrs post-dose), 22 (pre-dose), 43 (pre-dose) and 64 (pre-dose) of treatment, at end of treatment and 90 days post last dose;

For Q4W dosing schedule: on days 1 (pre- and 1 hr post-dose), 2 (24 hrs post-dose), 29 (pre-dose), 57 (pre-dose) and 85 (pre-dose) of treatment, at end of treatment and 90 days post last dose.

2.5. Clinical Activity

The clinical activity of Antibody 1 will be evaluated as a composite assessment including objective response rate (ORR), disease control rate (DCR), duration of response (DoR), and progression-free survival (FPS), and assessed at the following timepoints:

For Q2W and Q4W dosing schedules: on days 57 and 113 of treatment and 8 weeks from end of treatment;

For Q3W dosing schedules: on day 64 of treatment and 8 weeks from end of treatment.

3. Results

As of the data cut-off date, 20 patients had received at least 1 dose of Antibody 1 across various dosing schedules. 5 patients remained on study and 2 patients discontinued due to adverse events. There were no DLTs or adverse events resulting in death.

Figure 2A:
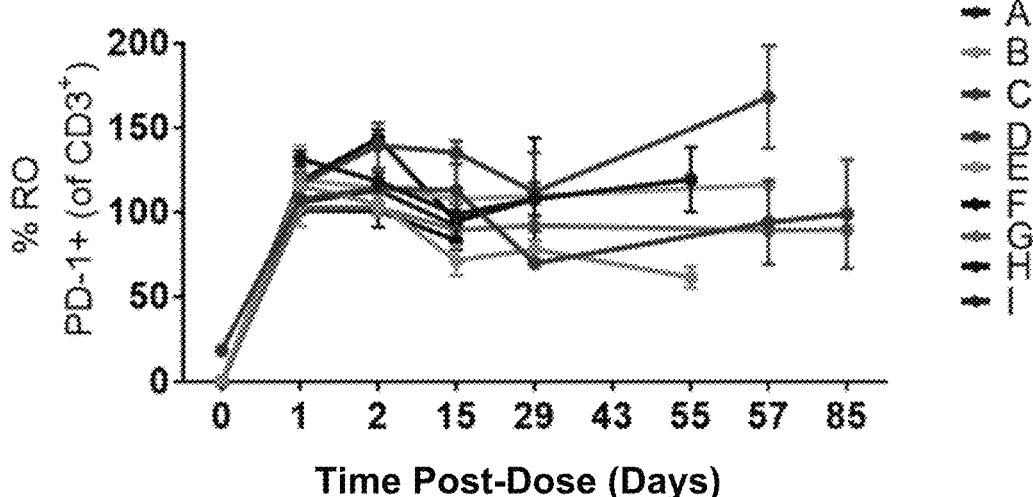
FIG. 2A plots the percent receptor occupancy of Antibody 1 determined using the saturation binding method. Subjects A-C(80 mg Q2W) subjects D-I (240 mg Q2W).
Figure 2B:
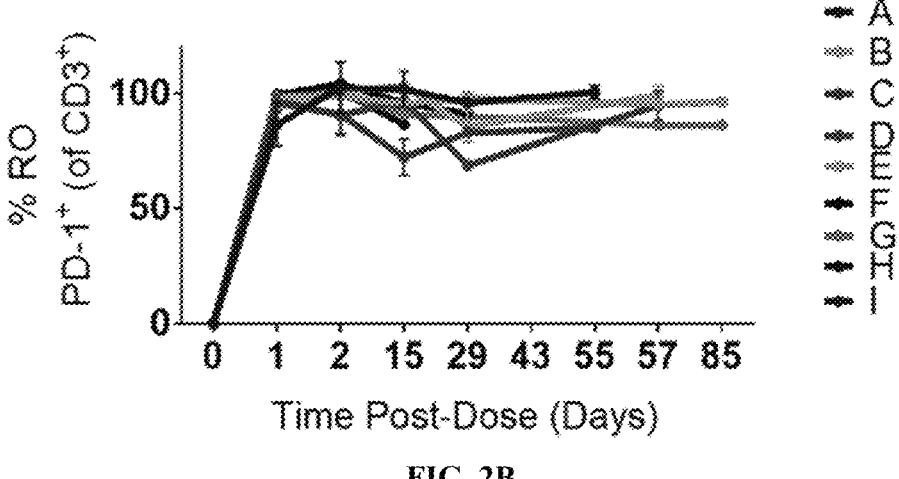
FIG. 2B plots the percent receptor occupancy of Antibody 1 determined using the competitive assay method. Subjects A-C(80 mg Q2W) subjects D-I (240 mg Q2W).

Receptor occupancy data from peripheral blood mononuclear cells were obtained from 3 patients in the 80 mg Q2W cohort and 6 patients in the 240 mg Q2W cohort. Receptor occupancy of participating patients was evaluated using 2 methods: (1) saturation binding (using a biotinylated anti-hIgG4 for the detection of Antibody 1, by a previously published method: Brahmer J R, Drake C G, Wollner I, et al. Phase I study of single-agent anti-programmed death-1 (MDX-1106) in refractory solid tumors: safety, clinical activity, pharmacodynamics, and immunologic correlates. *J Clin Oncol.* 2010; 28(19):3167-75) and (2) direct competition (via commercially available anti PD-1 antibody) that is competitive with Antibody 1. As seen in FIG. 2A and FIG. 2B, data from the nine patients showed PK levels greater than ~10 nM had ≥80% receptor occupancy using both methods. One patient each in the 80 and 240 mg Q2W cohorts had a receptor occupancy <80% as measured by at least 1 method.

Sixteen patients were response-evaluable. Disease control rate was 50% in all-corner population and two patients demonstrated a reduction in tumor lesion size from screening. The two individuals were a head and neck cancer patient in the 80 mg Q2W cohort and an ovarian cancer patient in the 360 mg Q2W cohort.

These results support several dosing regimens for Antibody 1 in patients with solid tumors.

4. List of References

Agata Y, Kawasaki A, Nishimura H, et al. Expression of the PD-1 antigen on the surface of stimulated mouse T and B lymphocytes. Int Immunol. 1996; 8:765-72.

BAVENCIO (avelumab) injection [package insert]. New York, NY: EMD Serono, Inc and Pfizer, Inc.; May 2017.

Bennett F, Luxenberg D, Ling V, et al. Program death-1 engagement upon TCR activation has distinct effects on costimulation and cytokine-driven proliferation: attenuation of ICOS, IL-4, and IL-21, but not CD28, IL-7, and IL-15 responses. J Immunol. 2003; 170:711-8.

Blank C, Gajewski T F, Mackensen A. Interaction of PD-L1 on tumor cells with PD-1 on tumor-specific T cells as a mechanism of immune evasion: implications for tumor immunotherapy. Cancer immunology, immunotherapy: CII. 2005; 54:307-14.

Carter L, Fouser L A, Jussif J, et al. PD-1: PD-L inhibitory pathway affects both CD4 (+) and CD8 (+) T cells and is overcome by IL-2. Eur J Immunol. 2002; 32:634-43.

Dong H, Strome S E, Salomao D R, et al. Tumor-associated B7-H1 promotes T-cell apoptosis: a potential mechanism of immune evasion. Nat Med. 2002; 8:793-800.

Dong H, Chen L. B7-H1 pathway and its role in the evasion of tumor immunity. J Mol Med (Berl). 2003; 81:281-7.

Eisenhauer E A, Therasse P, Bogaerts J, et al. New response evaluation criteria in solid tumours: revised RECIST guidelines (version 1.1). Eur J Cancer. 2009; 45:228-47.

Food and Drug Administration (FDA). Modification of the dosage regimen for nivolumab; September 2016. Available at: https://www.fda.gov/drugs/informationondrugs/approveddrugs/ucm520871.htm.

Freeman G J, Long A J, Iwai Y, et al. Engagement of the PD-1 immunoinhibitory receptor by a novel B7 family member leads to negative regulation of lymphocyte activation. J Exp Med. 2000; 192:1027-34.

IMFINZI (durvalumab) injection [package insert]. Wilmington, D E: AstraZeneca Pharmaceuticals LP; May 2017.

KEYTRUDA (pembrolizumab) injection [package insert]. Whitehouse Station, N J: Merck Sharpe & Dohme Corp., a subsidiary of Merck & Co, Inc.; May 2017.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating a solid tumor, comprising administering to a subject in need thereof an antibody or antigen binding fragment thereof in a flat dose of 80 mg to 360 mg once every two weeks intravenously, said antibody or antigen binding fragment thereof comprising a heavy chain variable region comprising SEQ ID NO: 53; a light chain variable region comprising SEQ ID NO: 67; and a human constant region of IgG4 isotype.

2. The method of claim 1, wherein said antibody or antigen binding fragment thereof is administered in a flat dose of 240 mg once every two weeks.

3. The method of claim 1, wherein said antibody or antigen binding fragment thereof is administered in a flat dose of 360 mg once every two weeks.

4. The method of claim 1, wherein said intravenous administration occurs over a period of 0.1 to 2 hours.

5. The method of claim 1, wherein said intravenous administration occurs over a period of 0.1 to 1 hours.

6. The method of claim 1, wherein the solid tumor is selected from the group consisting of non-small-cell lung cancer, gastric carcinoma, squamous cell carcinoma of the head and neck, renal cell carcinoma, esophageal cancer, breast cancer, colorectal cancer, prostate cancer, melanoma, bladder cancer, ovarian cancer, endometrial cancer, Merkel cell carcinoma, and gastroesophageal cancer.

7. A method of treating a solid tumor, comprising administering to a subject in need thereof an antibody or antigen binding fragment thereof comprising a heavy chain variable region comprising SEQ ID NO: 53; a light chain variable region comprising SEQ ID NO: 67; and a human constant region of IgG4 isotype, wherein said antibody or antigen binding fragment thereof is administered intravenously in a flat dose of 240 mg once every two weeks, 360 mg once every three weeks, or is 480 mg once every four weeks.

8. The method of claim 7, wherein said antibody or antigen binding fragment thereof is administered intravenously in a flat dose of 240 mg once every two weeks.

9. The method of claim 7, wherein said antibody or antigen binding fragment thereof is administered intravenously in a flat dose of 360 mg once every three weeks.

10. The method of claim 7, wherein said antibody or antigen binding fragment thereof is administered intravenously in a flat dose of 480 mg once every four weeks.

11. The method of claim 7, wherein said intravenous administration occurs over a period of 0.1 to 2 hours.

12. The method of claim 7, wherein said intravenous administration occurs over a period of 0.1 to 1 hours.

13. The method of claim 7, wherein the solid tumor is an advanced solid tumor.

14. The method of claim 7, wherein the solid tumor is selected from the group consisting of non-small-cell lung cancer, gastric carcinoma, squamous cell carcinoma of the head and neck, renal cell carcinoma, esophageal cancer, breast cancer, colorectal cancer, prostate cancer, melanoma, bladder cancer, ovarian cancer, endometrial cancer, Merkel cell carcinoma, and gastroesophageal cancer.

15. The method of claim 7, wherein the solid tumor is non-small cell lung cancer, gastric carcinoma, esophageal cancer, gastroesophageal cancer, or squamous cell carcinoma of the head and neck.

16. The method of claim 7, wherein the solid tumor is squamous cell carcinoma of the head and neck or ovarian cancer.

17. The method of claim 1, wherein the solid tumor is non-small cell lung cancer, gastric carcinoma, esophageal cancer, gastroesophageal cancer, or squamous cell carcinoma of the head and neck.

18. The method of claim 1, wherein the solid tumor is squamous cell carcinoma of the head and neck or ovarian cancer.

*     *     *     *     *

```
                         SEQUENCE LISTING

Sequence total quantity: 68
SEQ ID NO: 1              moltype = AA   length = 7
FEATURE                   Location/Qualifiers
source                    1..7
                          mol_type = protein
                          organism = Homo sapiens
SEQUENCE: 1
STTYYWV                                                         7

SEQ ID NO: 2              moltype = DNA   length = 21
FEATURE                   Location/Qualifiers
source                    1..21
                          mol_type = other DNA
                          organism = Homo sapiens
SEQUENCE: 2
agtactactt actactgggt c                                         21

SEQ ID NO: 3              moltype = AA   length = 16
FEATURE                   Location/Qualifiers
source                    1..16
                          mol_type = protein
                          organism = Homo sapiens
SEQUENCE: 3
SISYSGNTYY NPSLKS                                               16

SEQ ID NO: 4              moltype = DNA   length = 48
FEATURE                   Location/Qualifiers
source                    1..48
                          mol_type = other DNA
                          organism = Homo sapiens
SEQUENCE: 4
agtatctctt atagtgggaa cacctactac aatccgtccc tcaagagt            48

SEQ ID NO: 5              moltype = AA   length = 13
FEATURE                   Location/Qualifiers
source                    1..13
                          mol_type = protein
                          organism = Homo sapiens
SEQUENCE: 5
HLGYNGRYLP FDY                                                  13

SEQ ID NO: 6              moltype = DNA   length = 39
FEATURE                   Location/Qualifiers
source                    1..39
                          mol_type = other DNA
                          organism = Homo sapiens
SEQUENCE: 6
catctagggt ataatgggag gtacctcccc tttgactac                      39

SEQ ID NO: 7              moltype = AA   length = 14
FEATURE                   Location/Qualifiers
source                    1..14
```

```
                            mol_type = protein
                            organism = Homo sapiens
SEQUENCE: 7
TGTSSDVGFY NYVS                                              14

SEQ ID NO: 8               moltype = DNA   length = 42
FEATURE                    Location/Qualifiers
source                     1..42
                           mol_type = other DNA
                           organism = Homo sapiens
SEQUENCE: 8
actggaacca gcagtgacgt tggtttttat aactatgtct cc               42

SEQ ID NO: 9               moltype = AA   length = 7
FEATURE                    Location/Qualifiers
source                     1..7
                           mol_type = protein
                           organism = Homo sapiens
SEQUENCE: 9
DVTNRPS                                                      7

SEQ ID NO: 10              moltype = DNA   length = 21
FEATURE                    Location/Qualifiers
source                     1..21
                           mol_type = other DNA
                           organism = Homo sapiens
SEQUENCE: 10
gatgtcacta atcggccctc a                                      21

SEQ ID NO: 11              moltype = AA   length = 10
FEATURE                    Location/Qualifiers
source                     1..10
                           mol_type = protein
                           organism = Homo sapiens
SEQUENCE: 11
SSYTSISTWV                                                   10

SEQ ID NO: 12              moltype = DNA   length = 30
FEATURE                    Location/Qualifiers
source                     1..30
                           mol_type = other DNA
                           organism = Homo sapiens
SEQUENCE: 12
agctcatata caagcatcag cacttgggtg                             30

SEQ ID NO: 13              moltype = AA   length = 7
FEATURE                    Location/Qualifiers
source                     1..7
                           mol_type = protein
                           organism = Homo sapiens
SEQUENCE: 13
SSTYYWG                                                      7

SEQ ID NO: 14              moltype = DNA   length = 21
FEATURE                    Location/Qualifiers
source                     1..21
                           mol_type = other DNA
                           organism = Homo sapiens
SEQUENCE: 14
agtagtactt actactgggg c                                      21

SEQ ID NO: 15              moltype = AA   length = 16
FEATURE                    Location/Qualifiers
source                     1..16
                           mol_type = protein
                           organism = Homo sapiens
SEQUENCE: 15
SISYSGSTYY NPSLKS                                            16

SEQ ID NO: 16              moltype = DNA   length = 48
FEATURE                    Location/Qualifiers
source                     1..48
                           mol_type = other DNA
                           organism = Homo sapiens
SEQUENCE: 16
agtatctctt atagtgggag cacctactac aatccgtccc tcaagagt         48

SEQ ID NO: 17              moltype = AA   length = 7
FEATURE                    Location/Qualifiers
```

-continued

```
source                    1..7
                          mol_type = protein
                          organism = Homo sapiens
SEQUENCE: 17
DVSNRPS                                                                    7

SEQ ID NO: 18             moltype = DNA   length = 21
FEATURE                   Location/Qualifiers
source                    1..21
                          mol_type = other DNA
                          organism = Homo sapiens
SEQUENCE: 18
gatgtcagta atcggccctc a                                                    21

SEQ ID NO: 19             moltype = AA   length = 10
FEATURE                   Location/Qualifiers
source                    1..10
                          mol_type = protein
                          organism = Homo sapiens
SEQUENCE: 19
SSYTNISTWV                                                                 10

SEQ ID NO: 20             moltype = DNA   length = 30
FEATURE                   Location/Qualifiers
source                    1..30
                          mol_type = other DNA
                          organism = Homo sapiens
SEQUENCE: 20
agctcatata caaacatcag cacttgggtg                                           30

SEQ ID NO: 21             moltype = AA   length = 7
FEATURE                   Location/Qualifiers
source                    1..7
                          mol_type = protein
                          organism = Homo sapiens
SEQUENCE: 21
STTYYWG                                                                    7

SEQ ID NO: 22             moltype = DNA   length = 21
FEATURE                   Location/Qualifiers
source                    1..21
                          mol_type = other DNA
                          organism = Homo sapiens
SEQUENCE: 22
agtactactt actactgggg c                                                    21

SEQ ID NO: 23             moltype = AA   length = 16
FEATURE                   Location/Qualifiers
source                    1..16
                          mol_type = protein
                          organism = Homo sapiens
SEQUENCE: 23
SISYSGTTYY NPSLKS                                                          16

SEQ ID NO: 24             moltype = DNA   length = 48
FEATURE                   Location/Qualifiers
source                    1..48
                          mol_type = other DNA
                          organism = Homo sapiens
SEQUENCE: 24
agtatctctt atagtgggac cacctactac aacccgtccc tcaagagt                       48

SEQ ID NO: 25             moltype = AA   length = 13
FEATURE                   Location/Qualifiers
source                    1..13
                          mol_type = protein
                          organism = Homo sapiens
SEQUENCE: 25
HLGYNSNWYP FDY                                                             13

SEQ ID NO: 26             moltype = DNA   length = 39
FEATURE                   Location/Qualifiers
source                    1..39
                          mol_type = other DNA
                          organism = Homo sapiens
SEQUENCE: 26
catctcgggt ataacagcaa ctggtaccct tttgactac                                 39

SEQ ID NO: 27             moltype = AA   length = 14
```

-continued

```
FEATURE                 Location/Qualifiers
source                  1..14
                        mol_type = protein
                        organism = Homo sapiens
SEQUENCE: 27
TGTSSDVGSY NRVS                                                    14

SEQ ID NO: 28           moltype = DNA   length = 42
FEATURE                 Location/Qualifiers
source                  1..42
                        mol_type = other DNA
                        organism = Homo sapiens
SEQUENCE: 28
actggaacca gcagtgacgt tggtagttat aaccgtgtct cc                     42

SEQ ID NO: 29           moltype = AA   length = 7
FEATURE                 Location/Qualifiers
source                  1..7
                        mol_type = protein
                        organism = Homo sapiens
SEQUENCE: 29
EVSNRPS                                                            7

SEQ ID NO: 30           moltype = DNA   length = 21
FEATURE                 Location/Qualifiers
source                  1..21
                        mol_type = other DNA
                        organism = Homo sapiens
SEQUENCE: 30
gaggtcagta atcggccctc a                                            21

SEQ ID NO: 31           moltype = AA   length = 10
FEATURE                 Location/Qualifiers
source                  1..10
                        mol_type = protein
                        organism = Homo sapiens
SEQUENCE: 31
SSYTSSSTWV                                                         10

SEQ ID NO: 32           moltype = DNA   length = 30
FEATURE                 Location/Qualifiers
source                  1..30
                        mol_type = other DNA
                        organism = Homo sapiens
SEQUENCE: 32
agctcatata caagcagcag cacttgggtg                                   30

SEQ ID NO: 33           moltype = AA   length = 5
FEATURE                 Location/Qualifiers
source                  1..5
                        mol_type = protein
                        organism = Homo sapiens
SEQUENCE: 33
SHAMS                                                              5

SEQ ID NO: 34           moltype = DNA   length = 15
FEATURE                 Location/Qualifiers
source                  1..15
                        mol_type = other DNA
                        organism = Homo sapiens
SEQUENCE: 34
agccatgcca tgagc                                                   15

SEQ ID NO: 35           moltype = AA   length = 17
FEATURE                 Location/Qualifiers
source                  1..17
                        mol_type = protein
                        organism = Homo sapiens
SEQUENCE: 35
TITGGGGSIY YADSVKG                                                 17

SEQ ID NO: 36           moltype = DNA   length = 51
FEATURE                 Location/Qualifiers
source                  1..51
                        mol_type = other DNA
                        organism = Homo sapiens
SEQUENCE: 36
actattactg gtggtggtgg tagcatatac tacgcagact ccgtgaaggg c           51
```

-continued

```
SEQ ID NO: 37            moltype = AA   length = 10
FEATURE                  Location/Qualifiers
source                   1..10
                         mol_type = protein
                         organism = Homo sapiens
SEQUENCE: 37
NRAGEGYFDY                                                     10

SEQ ID NO: 38            moltype = DNA   length = 30
FEATURE                  Location/Qualifiers
source                   1..30
                         mol_type = other DNA
                         organism = Homo sapiens
SEQUENCE: 38
aaccgcgctg gggaggggtta ctttgactac                             30

SEQ ID NO: 39            moltype = AA   length = 11
FEATURE                  Location/Qualifiers
source                   1..11
                         mol_type = protein
                         organism = Homo sapiens
SEQUENCE: 39
GGDNIGNKDV H                                                   11

SEQ ID NO: 40            moltype = DNA   length = 33
FEATURE                  Location/Qualifiers
source                   1..33
                         mol_type = other DNA
                         organism = Homo sapiens
SEQUENCE: 40
gggggagaca acattggaaa taaagatgtg cac                          33

SEQ ID NO: 41            moltype = AA   length = 7
FEATURE                  Location/Qualifiers
source                   1..7
                         mol_type = protein
                         organism = Homo sapiens
SEQUENCE: 41
RDSNRPS                                                        7

SEQ ID NO: 42            moltype = DNA   length = 21
FEATURE                  Location/Qualifiers
source                   1..21
                         mol_type = other DNA
                         organism = Homo sapiens
SEQUENCE: 42
agggatagca accggccctc t                                       21

SEQ ID NO: 43            moltype = AA   length = 8
FEATURE                  Location/Qualifiers
source                   1..8
                         mol_type = protein
                         organism = Homo sapiens
SEQUENCE: 43
QVWDSIWV                                                       8

SEQ ID NO: 44            moltype = DNA   length = 24
FEATURE                  Location/Qualifiers
source                   1..24
                         mol_type = other DNA
                         organism = Homo sapiens
SEQUENCE: 44
caggtgtggg acagcatttg ggtg                                    24

SEQ ID NO: 45            moltype = AA   length = 123
FEATURE                  Location/Qualifiers
source                   1..123
                         mol_type = protein
                         organism = Homo sapiens
SEQUENCE: 45
QLQLQESGPG LVKPSETLTL TCTVSGDSIS STTYYWVWIR QPPGKGLEWI GSISYSGNTY  60
YNPSLKSRVT ISVDTSKNHF SLKLSSVAAT DTALYYCARH LGYNGRYLPF DYWGQGTLVT 120
VSS                                                              123

SEQ ID NO: 46            moltype = DNA   length = 369
FEATURE                  Location/Qualifiers
source                   1..369
                         mol_type = other DNA
                         organism = Homo sapiens
```

```
SEQUENCE: 46
cagctgcagc tgcaggagtc gggcccagga ctggtgaagc cttcggagac cctgaccctc    60
acctgcactg tctctggtga ctccatcagc agtactactt actactgggt ctggatccgc   120
cagcccccag ggaagggact ggagtggatt gggagtatct cttatagtgg gaacacctac   180
tacaatccgt ccctcaagag tcgagtcacc atatccgtag acacgtccaa gaaccacttc   240
tccctgaagc tgagttctgt ggccgccaca gacacggctc tatattactg tgcgagacat   300
ctagggtata atgggaggta cctcccctt gactactggg gccagggaac cctggtcacc    360
gtctcctcc                                                           369

SEQ ID NO: 47               moltype = AA  length = 110
FEATURE                     Location/Qualifiers
source                      1..110
                            mol_type = protein
                            organism = Homo sapiens
SEQUENCE: 47
QSALTQPASV SGSPGQSITI SCTGTSSDVG FYNYVSWYQQ HPGKAPELMI YDVTNRPSGV    60
SDRFSGSKSG NTASLTISGL QAEDEADYYC SSYTSISTWV FGGGTKLTVL              110

SEQ ID NO: 48               moltype = DNA  length = 330
FEATURE                     Location/Qualifiers
source                      1..330
                            mol_type = other DNA
                            organism = Homo sapiens
SEQUENCE: 48
cagtctgccc tgactcagcc tgcctccgtg tctgggtctc ctggacagtc gatcaccatc    60
tcctgcactg gaaccagcag tgacgttggt ttttataact atgtctcctg gtaccaacag   120
cacccaggca aagcccccga actcatgatt tatgatgtca ctaatcggcc ctcaggggtt   180
tctgatcgct tctctggctc caagtctggc aacacggcct ccctgaccat ctctgggctc   240
caggctgagg acgaggctga ttattactgc agctcatata caagcatcag cacttgggtg   300
ttcggcggag ggaccaagct gaccgtccta                                    330

SEQ ID NO: 49               moltype = AA  length = 123
FEATURE                     Location/Qualifiers
source                      1..123
                            mol_type = protein
                            organism = Homo sapiens
SEQUENCE: 49
QLQLQESGPG LVKPSETLSL TCTVSGGSIS SSTYYWGWIR QPPGKGLEWI GSISYSGSTY    60
YNPSLKSRVT ISVDTSKNQF SLKLSSVTDA DTAVYYCARH LGYNGRYLPF DYWGQGTLVT   120
VSS                                                                 123

SEQ ID NO: 50               moltype = DNA  length = 369
FEATURE                     Location/Qualifiers
source                      1..369
                            mol_type = other DNA
                            organism = Homo sapiens
SEQUENCE: 50
cagctgcagc tgcaggagtc gggcccagga ctggtgaagc cttcggagac cctgtccctc    60
acctgcactg tctctggtgg ctccatcagc agtagtactt actactgggg ctggatccgc   120
cagcccccag ggaagggact ggagtggatt gggagtatct cttatagtgg gagcacctac   180
tacaatccgt ccctcaagag tcgagtcacc atatccgtag acacgtccaa gaaccagttc   240
tccctgaagc tgagctctgt gaccgacgca gacacggctg tgtattactg tgcgagacat   300
ctagggtata atgggaggta cctcccctt gactactggg gccagggaac cctggtcacc    360
gtctcctcc                                                           369

SEQ ID NO: 51               moltype = AA  length = 110
FEATURE                     Location/Qualifiers
source                      1..110
                            mol_type = protein
                            organism = Homo sapiens
SEQUENCE: 51
QSALTQPASV SGSPGQSITI SCTGTSSDVG FYNYVSWYQQ HPGKAPEVMI YDVSNRPSGV    60
SDRFSGSKSG NTASLTISGL QAEDEADYYC SSYTSISTWV FGGGTKLTVL              110

SEQ ID NO: 52               moltype = DNA  length = 330
FEATURE                     Location/Qualifiers
source                      1..330
                            mol_type = other DNA
                            organism = Homo sapiens
SEQUENCE: 52
cagtctgccc tgactcagcc tgcctccgtg tctgggtctc ctggacagtc gatcaccatc    60
tcctgcactg gaaccagcag tgacgttggt ttttataact atgtctcctg gtaccaacag   120
cacccaggca aagcccccga agtcatgatt tatgatgtca gtaatcggcc ctcaggggtt   180
tctgatcgct tctctggctc caagtctggc aacacggcct ccctgactat ctctgggctc   240
caggctgagg acgaggctga ttattactgc agctcatata caagcatcag cacttgggtg   300
ttcggcggag ggaccaagct gactgtccta                                    330

SEQ ID NO: 53               moltype = AA  length = 123
FEATURE                     Location/Qualifiers
```

```
source                   1..123
                         mol_type = protein
                         organism = Homo sapiens
SEQUENCE: 53
QLQLQESGPG LVKPSETLTL TCTVSADSIS STTYYWVWIR QPPGKGLEWI GSISYSGSTY   60
YNPSLKSRVT VSVDTSKNQF SLKLNSVAAT DTALYYCARH LGYNGRYLPF DYWGQGTLVT  120
VSS                                                                123

SEQ ID NO: 54            moltype = DNA   length = 369
FEATURE                  Location/Qualifiers
source                   1..369
                         mol_type = other DNA
                         organism = Homo sapiens
SEQUENCE: 54
cagctgcagc tgcaggagtc gggcccagga ctggtgaagc cttcggagac cctgaccctc   60
acctgcactg tctctgctga ctccatcagc agtactactt actactgggt ctggatccgc  120
cagcccccag ggaagggact ggagtggatt gggagtatct cttatagtgg gagcacctac  180
tacaatccgt ccctcaagag tcgagtcacc gtatccgtag acacgtccaa gaaccagttc  240
tccctgaagc tgaactctgt ggccgccaca gacacggctc tatattactg tgcgagacat  300
ctagggtata atgggaggta cctccccttt gactactggg gccagggaac cctggtcacc  360
gtctcctcc                                                          369

SEQ ID NO: 55            moltype = AA   length = 110
FEATURE                  Location/Qualifiers
source                   1..110
                         mol_type = protein
                         organism = Homo sapiens
SEQUENCE: 55
QSALTQPASV SGSPGQSITI SCTGTSSDVG FYNYVSWYQQ HPGKAPELMI YDVSNRPSGV   60
SDRFSGSKSG NTASLTISGL QAEDEADYYC SSYTNISTWV FGGGTKLTVL              110

SEQ ID NO: 56            moltype = DNA   length = 330
FEATURE                  Location/Qualifiers
source                   1..330
                         mol_type = other DNA
                         organism = Homo sapiens
SEQUENCE: 56
cagtctgccc tgactcagcc tgcctccgtg tctgggtctc ctggacagtc gatcaccatc   60
tcctgcactg gaaccagcag tgacgttggt ttttataact atgtctcctg gtaccaacag  120
cacccaggca aagcccccga actcatgatt tatgatgtca gtaatcggcc ctcaggggtt  180
tctgatcgct tctctggctc caagtctggc aacacggcct ccctgaccat ctctgggctc  240
caggctgagg acgaggctga ttattactgc agctcatata caaacatcag cacttgggtg  300
ttcggcggag ggaccaagct gaccgtccta                                   330

SEQ ID NO: 57            moltype = AA   length = 123
FEATURE                  Location/Qualifiers
source                   1..123
                         mol_type = protein
                         organism = Homo sapiens
SEQUENCE: 57
QLQLQESGPG LVKPSETLSL TCTVSGGSIS STTYYWGWIR QPPGKGLEWI GSISYSGTTY   60
YNPSLKSRVT IPVDTSKNQI SLKLSSVTAA DTSLYYCARH LGYNSNWYPF DYWGQGTLVT  120
VSS                                                                123

SEQ ID NO: 58            moltype = DNA   length = 369
FEATURE                  Location/Qualifiers
source                   1..369
                         mol_type = other DNA
                         organism = Homo sapiens
SEQUENCE: 58
cagctgcagc tgcaggagtc gggcccagga ctggtgaagc cctcggagac cctgtccctc   60
acctgcactg tctctggtgg ctccatcagc agtactactt actactgggg ctggatccgc  120
cagcccccag ggaaggggct ggagtggatt gggagtatct cttatagtgg gaccacctac  180
tacaacccgt ccctcaagag tcgagtcacc atccccgtag acacgtccaa gaaccagatc  240
tccctgaaac tgagctctgt gaccgccgca gacacgtctt tgtattattg tgcgagacat  300
ctcgggtata acagcaactg gtaccctttt gactactggg gccagggaac cctggtcacc  360
gtctcctca                                                          369

SEQ ID NO: 59            moltype = AA   length = 110
FEATURE                  Location/Qualifiers
source                   1..110
                         mol_type = protein
                         organism = Homo sapiens
SEQUENCE: 59
QSALTQPPSV SGSPGQSVTI SCTGTSSDVG SYNRVSWYQQ PPGTAPEVII YEVSNRPSGV   60
PDRFSGSKSG NTASLTISGL QAEDEADYYC SSYTSSSTWV FGGGTKLTVL              110

SEQ ID NO: 60            moltype = DNA   length = 330
FEATURE                  Location/Qualifiers
```

```
source                  1..330
                        mol_type = other DNA
                        organism = Homo sapiens
SEQUENCE: 60
cagtcggccc tgactcagcc tccctccgtg tccgggtctc ctggacagtc agtcaccatc   60
tcctgcactg gaaccagcag tgacgttggt agttataacc gtgtctcctg gtaccagcag  120
cccccaggca cagcccccga agtcattatt tatgaggtca gtaatcggcc ctcaggggtc  180
cctgatcgct tctctgggtc caagtctggc aacacggcct ccctgaccat ctctgggctc  240
caggctgagg acgaggctga ttattactgc agctcatata caagcagcag cacttgggtg  300
ttcggcggag ggaccaagct gaccgtccta                                   330

SEQ ID NO: 61          moltype = AA   length = 119
FEATURE                Location/Qualifiers
source                 1..119
                       mol_type = protein
                       organism = Homo sapiens
SEQUENCE: 61
EVQLLESGGG LVQPGGSLRL SCAASGFTFS SHAMSWVRQA PGKGLEWVST ITGGGGSIYY   60
ADSVKGRFTI SRDNSKNTLY LQMNSLRAED TAVYYCAKNR AGEGYFDYWG QGTLVTVSS    119

SEQ ID NO: 62          moltype = DNA   length = 357
FEATURE                Location/Qualifiers
source                 1..357
                       mol_type = other DNA
                       organism = Homo sapiens
SEQUENCE: 62
gaggtgcagc tgttggagtc tgggggaggc ttggtacagc ctggggggtc cctgagactg   60
tcctgcgcag cctctggatt caccttagc agccatgcca tgagctgggt ccgccaggct   120
ccagggaagg ggctggagtg ggtctcaact attactggtg gtggtggtag catatactac  180
gcagactccg tgaagggccg gttcaccatc tccagagaca attccaagaa cacgctgtat  240
ctgcaaatga acagcctgag agccgaggac acggccgtat attattgtgc gaaaaaccgc  300
gctggggagg gttactttga ctactgggc cagggaaccc tggtcaccgt ctcctca      357

SEQ ID NO: 63          moltype = AA   length = 105
FEATURE                Location/Qualifiers
source                 1..105
                       mol_type = protein
                       organism = Homo sapiens
SEQUENCE: 63
SYELTQPLSV SVALGQTARI TCGGDNIGNK DVHWYQQKPG QAPVLVIYRD SNRPSGIPEG   60
FSGSNSGNTA TLTISRAQAG DEADYYCQVW DSIWVFGGGT KLTVL                   105

SEQ ID NO: 64          moltype = DNA   length = 315
FEATURE                Location/Qualifiers
source                 1..315
                       mol_type = other DNA
                       organism = Homo sapiens
SEQUENCE: 64
tcctatgagc tgactcagcc actctcagtg tcagtggccc tgggacagac ggccaggatt   60
acctgtgggg gagacaacat tggaaataaa gatgtgcact ggtaccagca gaagccaggc  120
caggcccctg tgctggtcat ctatagggat agcaaccggc cctctgggat ccctgaggga  180
ttctctggct ccaactcggg gaacacggcc accctgacca tcagcagagc ccaagccggg  240
gatgaggctg actattactg tcaggtgtgg gacagcattt gggtgttcgg cggagggacc  300
aagctgaccg tccta                                                   315

SEQ ID NO: 65          moltype = AA   length = 10
FEATURE                Location/Qualifiers
REGION                 1..10
                       note = Synthesis
source                 1..10
                       mol_type = protein
                       organism = synthetic construct
SEQUENCE: 65
SSYTSISTWV                                                          10

SEQ ID NO: 66          moltype = DNA   length = 30
FEATURE                Location/Qualifiers
misc_feature           1..30
                       note = Synthesis
source                 1..30
                       mol_type = other DNA
                       organism = synthetic construct
SEQUENCE: 66
agctcatata caagcatcag cacttgggtg                                   30

SEQ ID NO: 67          moltype = AA   length = 110
FEATURE                Location/Qualifiers
REGION                 1..110
                       note = Synthesis
```

-continued

```
source                  1..110
                        mol_type = protein
                        organism = synthetic construct
SEQUENCE: 67
QSALTQPASV SGSPGQSITI SCTGTSSDVG FYNYVSWYQQ HPGKAPELMI YDVSNRPSGV   60
SDRFSGSKSG NTASLTISGL QAEDEADYYC SSYTSISTWV FGGGTKLTVL              110

SEQ ID NO: 68           moltype = DNA   length = 330
FEATURE                 Location/Qualifiers
misc_feature            1..330
                        note = Synthesis
source                  1..330
                        mol_type = other DNA
                        organism = synthetic construct
SEQUENCE: 68
cagtctgccc tgactcagcc tgcctccgtg tctgggtctc ctggacagtc gatcaccatc   60
tcctgcactg gaaccagcag tgacgttggt ttttataact atgtctcctg gtaccaacag  120
cacccaggca aagcccccga actcatgatt tatgatgtca gtaatcggcc ctcaggggtt  180
tctgatcgct tctctggctc caagtctggc aacacggcct ccctgaccat ctctgggctc  240
caggctgagg acgaggctga ttattactgc agctcatata caagcatcag cacttgggtg  300
ttcggcggag ggaccaagct gaccgtccta                                   330
```